(12) United States Patent
Kouvetakis et al.

(10) Patent No.: US 6,207,844 B1
(45) Date of Patent: Mar. 27, 2001

(54) COMPOUNDS AND METHODS FOR DEPOSITING PURE THIN FILMS OF GALLIUM NITRIDE SEMICONDUCTOR

(75) Inventors: John Kouvetakis; Jeff McMurran, both of Mesa, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/310,490

(22) Filed: May 12, 1999

(51) Int. Cl.$^7$ .............................. C07F 5/00; C01B 21/06
(52) U.S. Cl. ........................ 556/1; 423/409; 420/903
(58) Field of Search ................ 423/409; 252/62.3 R; 420/903; 556/1

(56) References Cited

U.S. PATENT DOCUMENTS 5,976,398 * 11/1999 Yagi .............................. 252/62.36 A

OTHER PUBLICATIONS

Strite et al., J. Vac. Sci. Technol. B 10:1237, 1992.
Nakamura et al., Jpn. J. Appl. Phys. 34:L797, 1995.
Newmayer et al., J. Am. Chem. Soc. 117:5893, 1995.
Miehr et al., Organometallics 15:2053, 1996.
Kouvetakis et al., Chem Mater. 1:476–478, 1989.
Atwood et al., J. Organomet. Chem. 394:C6–C8, 1990.
Lakhoita et al., Chem Mater. 7:546–552, 1995.
Janik et al., Chem. Mater. 8:2708–2711, 1996.
Hwang et al., Chem. Mater. 7:517–525, 1995.
Jegler et al., Chem. Mater. 10:2041–2043, 1998.
Kouvetakis et al., Inorg. Chem 36:1792, 1997.
McMurran et al., App. Phys. Lett. 69:203–205, 1996.
McMurran et al., J. Am. Chem. Soc. 120:5233–5237, 1998.
McMurran et al., J. Inorg. Chem. 57:6636–6644, 1998.
McMurran et al., Appl. Phys. Lett. 74:1–4, 1999.
Neumayer et al., Chem Mater. 8:9–25, 1996.
Shirk et al., Inorganic Synthesis 17:45–47, 1978.
Hoffman–Bang et al., Acta Chem. Scand. 11:581, 1957.
Muller et al., Z anorg. Allg. Chem. 348:261, 1966.
Muller et al., J. Organomet. Chem. 12:37, 1968.
Goode et al., J. Chem. Soc. Chem. Commun. 768, 1988.
Baxter et al., Chem. Soc. Dalton, Trans. 807, 1985.
Harrison et al., Chem. Soc. Dalton 1554, 1972.
Dechnicke et al., Z. anorg. Allg. Chem. 444:71, 1978.
Janik et al., Inorg. Chem. 36:4135, 1997.
Thayer et al., Inorg. Chem. 4:1114, 1965.
Von Wiberg et al., Z. Annorg. allg. Chem. 394:197, 1972 No English Abstract.
Balasubramanian et al., Chem. Phys. Lett. 164:231, 1989.
Xi et al., J. Am. Chem. Soc. 120:3773, 1998.
Pulham et al., J. Am Chem. Soc. 113:5149–5162, 1991.
Downs et al., J. Am Chem. Soc. 111:1936–1937, 1989.
Lahiri et al., Appl. Phys. Lett., 67:1244, 1995.
Frank et al., Am. Chem. Soc., 120:3512, 1998.

* cited by examiner

Primary Examiner—Mark Kopec
(74) Attorney, Agent, or Firm—Baker Botts L.L.P.

(57) ABSTRACT

The invention is directed to novel compounds which serve as single-source precursors for the deposition of gallium nitride on thin films. The invention is also directed to methods for the synthesis of these novel compounds. The invention is further directed to methods for the use of such compounds in the deposition of gallium nitride on thin films and in the synthesis of bulk materials.

5 Claims, 18 Drawing Sheets

US 6,207,844 B1

COMPOUNDS AND METHODS FOR DEPOSITING PURE THIN FILMS OF GALLIUM NITRIDE SEMICONDUCTOR

BACKGROUND OF THE INVENTION

The importance of gallium nitride (GaN) and related wide bandgap nitrides in the successful fabrication of light emitting diodes and semiconductor lasers has prompted considerable research into their growth and development as described in Strite et al., J. Vac. Sci. Technol.B 10:1237, 1992; Nakamura et al., Jpn. J. Appl. Phys. 34:L797, 1995; Jones et al., Chem. Vap. Deposition 65, 1995. The concept of single source compounds containing the $N_3$ group has been extensively applied in recent years both in the US and Europe to prepare bulk powder and thin film material exhibiting interesting optical properties such as blue shifted light emissions.

Currently, the most common route to deposition of GaN by chemical vapor deposition (CVD) employs reactions of $(CH_3)_3Ga$ and $(C_2H_5)_3Ga$ with large excess of ammonia at temperatures in excess of 1000° C. as described in Neumayer et al., Chem. Mater. 8:9, 1996. The high thermal stability of the N—H bond in $NH_3$ necessitates deposition at extremely high temperatures.

Other azide-containing compounds that have been utilized to deposit GaN films contain organic groups. Unfortunately, the use of such compounds in many cases lead to unintentional incorporation of carbon impurities as described in Lakhoita et al., J. Chem. Mater. 3:441, 1995; Newmayer et al., J. Am. Chem. Soc. 117:5893, 1995; Muehr et al., Organometallics 15:2053, 1996.

A precursor of simplicity and low formula weight which has been used to generate GaN films is the well known $H_2GaNH_2$ compound as described in Hwang et al., Chem. Mater. 7:517(1995). However, this material is polymeric in the solid state and thus unsuitable for GaN film growth. Furthermore, it has been established that the extremely stable N—H bonds in the compound facilitate loss of $NH_3$ during its thermal decomposition to yield non-stoichiometric nitride material of composition $GaN_{0.83}$.

Other precursor compounds which have been used to generate gallium nitride films include diethylgallium azide as described in Kouvatekis et al., Chem. Mater. 1:476–478, 1989; Atwood et al., J. Organomet. Chem. 394:C6–C8, 1990; Lakhotia et al., Chem. Mater. 7:546–552, 1995; gallium imide as described in Janik et al., Chem. Mater. 8:2708–2711, 1996; and cyclotrigallazane as described in Hwang et al., Chem. Mater 7:517–525, 1995; Jegler et al., Chem Mater. 10:2041–2043, 1998.

Previous studies as reported in Kouvetakis et al., Inorg. Chem 36:1792, 1997; Kouvetakis et al., Chem. of Mat. 1:476, 1989, both incorporated by reference herein have demonstrated that the decomposition of an exclusively inorganic precursor, $Cl_2GaN_3$, leads to thin, oriented GaN layers on (100) Si substrates and heteroepitaxial films on basal plane sapphire at 700° C. The probable decomposition pathway for this precursor is demonstrated by the following equation:

$(Cl_2GaN_3)_3 \rightarrow GaN + 2GaCl_3 + 4N_2$.

The development of this compound demonstrated that a single source inorganic precursor could lead to the formation of single-crystalline GaN at low temperatures and at exceptionally high growth rates by conventional low-pressure deposition techniques as described in McMurran et al., App. Phys. Lett. 69:203–205, 1996, incorporated by reference herein.

Alternative synthetic methods based on single source molecular precursors that incorporate direct Ga—N bonds and labile, preferably, non-organic leaving groups offer the potential of significant improvements in film quality and growth process. Some of these benefits include lower deposition temperature, elimination of the inefficient use of ammonia, reduction in nitrogen vacancies and carbon contamination, and much enhanced doping capabilities.

It is desirable that optimal precursor compounds provide a facile decomposition pathway leading to the desirable material and be sufficiently volatile at room temperature to be applicable for chemical vapor deposition (CVD) or molecular beam epitaxy (MBE). However, most reported single source precursors are polynuclear species with very low vapor pressure which makes them unsuitable, or at best makes their use inconvenient, for CVD.

SUMMARY OF THE INVENTION

Accordingly, it is an object of the present invention to provide single source precursor compounds which allow the deposition of GaN at low temperatures and allow stoichiometric deposition of GaN onto thin films.

These and other objects of the invention are achieved by providing a compound having the general formula $(X_1X_2GaN_3)n$ wherein $X_1$ and $X_2$ can be the same or different and are selected from the group consisting of hydrogen and isotopes thereof, $CH_3$, F, Cl, Br, F and I wherein when $X_1$ is $CH_3X_2$ is H, and wherein n=1, 2, 3 or 4.

The invention is also directed to methods for the synthesis of these novel compounds. The invention is further directed to methods for the use of such compounds in the deposition of gallium nitride on thin films and in the synthesis of bulk materials.

BRIEF DESCRIPTION OF THE DRAWINGS

Further objects and advantages of the present invention will be more fully appreciated from a reading of the detailed description when considered with the accompanying drawings wherein.

DETAILED DESCRIPTION OF THE INVENTION

Figure 1:
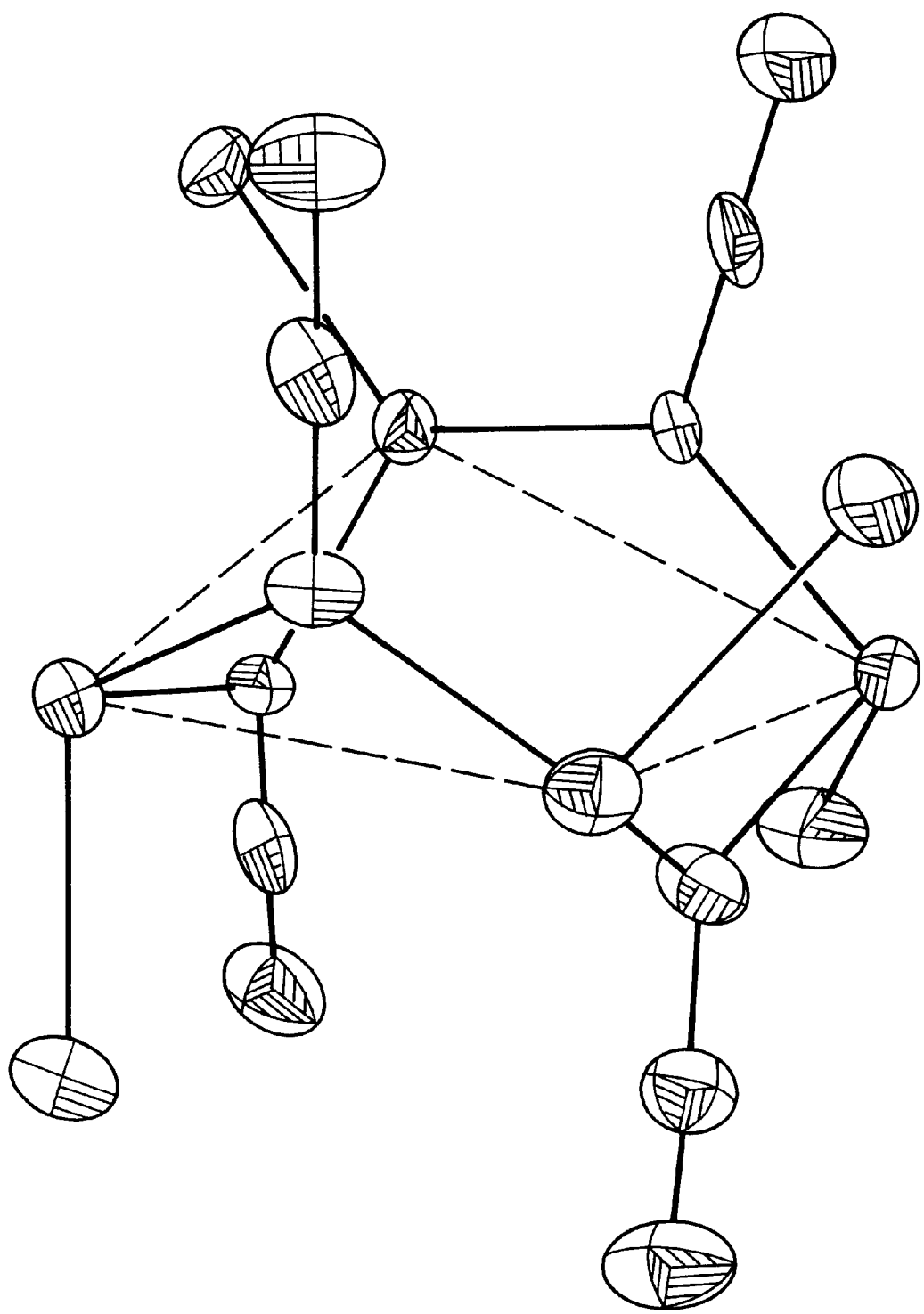
FIG. 1 is an illustration of the molecular structure of the azidochlorogallane $[ClHGaN_3]_4$.

The invention provides novel compounds which function as single-source precursors for the deposition of GaN on thin films. Preferred single-source precursors of the invention include H$_2$GaN$_3$, HClGaN$_3$, HBrGaN$_3$, Cl$_2$GaN$_3$, H(CH$_3$)GaN$_3$ and their derivatives, with H$_2$GaN$_3$ being the most preferred as described in McMurran et al., J. Am. Chem. Soc. 120:5233–5237, 1998; McMurran et al., J. Inorg. Chem. 57: 6636–6644, 1998; McMurran et al., Appl. Phys. Lett. 74:1–4, 1999, all incorporated by reference herein.

Preferred single source precursor compounds of the invention have the following formula(s):

$$(X_1X_2GaN_3)_n$$

wherein X$_1$ and X$_2$ can be the same or different and are selected from the group consisting of hydrogen and isotopes thereof, CH$_3$, Cl, Br, F and I wherein when X$_1$ is CH$_3$X$_2$ is H.

The invention also provides for the deposition of a GaN film wherein a single source precursor compound in accordance with the invention is contacted with a substrate of interest under conditions in which the single source compound decomposes to form GaN on the substrate. Typically, the precursor is held in a glass container at room temperature. The glass container is directly connected with a high vacuum valve to CVD-compatible reaction chamber including a substrate heated to a temperature of between 250 and 800° C. The vapor of the precursor is allowed to flow into the reaction which is typically maintained at a base pressure of 10$^{-10}$ Torr by a pump. Under these conditions the precursor decomposes and deposits a GaN film onto the substrate.

Suitable substrates for use in the invention are well known to those in the art and include but are not limited to sapphire, silica, silicon carbide and lithium gallate. An advantage of the present invention is that substrates which cannot be utilized at high temperatures can be accommodated by the low temperature processes of the invention.

In the most preferred embodiment of the invention, the single source precursor compound used to create GaN films is H$_2$GaN$_3$. H$_2$GaN$_3$ incorporates the lightest possible element H as a ligand in the molecular structure and also has the potential to eliminate extremely stable and benign species such as H$_2$ and N$_2$ byproducts to yield stoichiometric GaN free of carbon impurities. In addition, H$_2$GaN$_3$ does not contain heavy organic groups which invariably introduce carbon contamination during film growth, or N—H bonds which promote loss of nitrogen as NH$_3$. H$_2$GaN$_3$ is an air-sensitive liquid, highly energetic and reactive, but remarkably volatile and stable at room temperature. Most importantly, its decomposition reactions, often initiated at room temperature, yield pure GaN heterostructures and nanostructures of unusual morphologies and microstructure.

The HClGaN$_3$, and HBrGaN$_3$ compounds also offer a new very low temperature method for synthesizing GaN with unusual nanosize morphologies. In another embodiment of the invention, HCH$_3$GaN$_3$, is provided as a precursor compound. This compound is less reactive, i.e., more inert, than H$_2$GaN$_3$ and thus easier to handle and store. It is a volatile liquid having a boiling point of 50° C. at 0.20 torr is readily distilled and purified without decomposition, and can be used for the deposition of GaN according to the following reaction:

HCH$_3$GaN$_3$→CH$_4$+N$_2$+GaN

Crystalline HClGaN$_3$ is a moderately volatile molecular system consisting of interconnected tetrameric Ga$_4$N$_4$ units that have a conformation similar to cyclooctane. The compound in the vapor phase consists of (HClGaN$_3$)$_3$ trimers which decompose readily at low temperatures by elimination of HCl and N$_2$ to grow GaN layers on sapphire and Si substrates. Solid [HClGaN$_3$]$_4$ decomposes exothermically near its melting point, i.e., 70° C., to yield nanocrystalline GaN bulk material.

The invention further provides methods for the synthesis of the single source precursor compounds of the invention. In one embodiment of the invention, the precursor HClGaN$_3$ is preferably synthesized according to the following reaction:

HGaCl$_2$+LiN$_3$→HClGaN$_3$+LiCl via a metathesis reaction involving HGaCl$_2$ and LiN$_3$.

The invention is also directed to methods for the synthesis of the precursor compound H$_2$GaN$_3$. In one embodiment of the invention, H$_2$GaN$_3$ is synthesized according to the following reaction:

H$_2$GaCl+LiN$_3$→H$_2$GaN$_3$+LiCl

In a preferred embodiment of the invention, H$_2$GaN$_3$, HBrGaN$_3$ and D$_2$GaN$_3$ are synthesized via reduction of Br$_2$GaN$_3$ with an excess of LiGaH$_4$. The synthetic reaction series for this method of synthesis is illustrated by the following reactions:

GaBr$_3$+SiMe$_3$N$_3$→SiMe$_3$N$_3$.GaBr$_3$

SiMe$_3$N$_3$.GaBr$_3$→SiMe$_3$Br+Br$_2$GaN$_3$

Br$_2$GaN$_3$+LiGaH$_4$→HBrGaN$_3$+LiBr+GaH$_3$

Br$_2$GaN$_3$+2LiGaH$_4$→H$_2$GaN$_3$+2LiBr+2GaH$_3$

Br$_2$GaN$_3$+2LiGaD$_4$→D$_2$GaN$_3$+2LiBr+2GaD$_3$

The invention also provides a method for the synthesis of HCH$_3$GaN$_3$ according to the following reaction:

CH$_3$GaCl$_2$+SiMe$_3$N$_3$→CH$_3$ClGaN$_3$+SiMe$_3$Cl

CH$_3$ClGaN$_3$+LiGaH$_4$→CH$_3$HGaN$_3$+LiCl+GaH$_3$

GaN exists in at least two different crystalline polymorphs: wurtzite and zincblende structures (Neumayer et al., Chem Mater. 8:9–25, 1996).

The single source precursor compounds of the invention allow for the deposition of GaN on thin films by techniques known to those skilled in the art, including, but not limited to chemical vapor deposition (CVD) or molecular beam epitaxy (MBE).

Film growth and analysis using the single source precursor compounds of the invention can be analyzed using standard techniques, including, but not limited to, the determination of film thickness, rate of deposition, transmission electron microscopy, transmission infrared analysis, Rutherford backscattering spectroscopy, X-ray diffraction, oxygen resonance reactions, secondary ion mass spectrometric analysis (SIMS) and Auger electron spectroscopy. Bulk materials can be analyzed using powder diffraction and photoluminescence studies.

The invention is further directed to methods for the generation of GaN nanocrystals and GaN deposition on thin films using $HClGaN_3$. Solid $HClGaN_3$ decomposes exothermically at the melting point, i.e., 70° C., to yield pure wurtzite and zincblende GaN nanocrystals and fibers that emit at 3.3 eV. In addition, vapor deposition studies have shown that the thermal decomposition of gaseous $HClGaN_3$ on sapphire substrates results in formation of stoichiometric GaN films at 500° C.

The present invention also provides a highly efficient method for growing GaN thin films at a temperature between 150–700° C. using $H_2GaN_3$ as a single source precursor compound. Uncommonly low temperature growth of nanocrystalline GaN films with the wurtzite structure is readily achieved at 150–200° C. from the thermodynamically driven decomposition of the precursor via complete elimination of $H_2$ and $N_2$ byproducts in accordance with the following reaction:

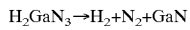

$H_2GaN_3 \rightarrow H_2 + N_2 + GaN$

The synthesis of GaN nanocrystals using $H_2GaN_3$ and the methods of the invention provides a very simple chemical route to thin films having simple quantum dot structures which may exhibit a blueshifted high energy emission, i.e., 4.0 eV. Highly-oriented columnar growth of crystalline material is obtained on Si at 350–700° C. and heteroepitaxial growth is readily achieved on sapphire at 650° C. Crucial advantages of this process include the significant vapor pressure of the precursor which permits rapid mass transport at low temperature, i.e., 22° C. and the facile decomposition pathway of stoichiometric elimination of $H_2$ and $N_2$ over a wide temperature and pressure range which allows film growth at very low temperatures and pressures, i.e., $10^{-4}$–$10^{-8}$ Torr, with growth rates up to 80 nm per minute. There are no simpler byproducts than $H_2$ and $N_2$.

From a practical view point, the method is obviously fully compatible with low pressure CVD methods ($10^{-6}$–$10^{-4}$ Torr), and a preferred embodiment of the invention is a method for the deposition of gallium nitride by CVD using $H_2GaN_3$. It is also compatible with molecular beam epitaxy (MBE) methods since acceptable nitride growth rates at pressures as low as $10^{-8}$ Torr are obtained from the room temperature vapor pressure of the precursor. The exothermic decomposition reaction of liquid $H_2GaN_3$ often initiated at room temperature yields crystalline microfibers up to several microns in length and 15–20 nm wide. In semiconductors, such morphologies have recently gained considerable attention because of potential uses in optoelectronics and nanodevices.

Based on the mass spectrum, $H_2GaN_3$ is a trimer in the vapor phase and decomposes readily at low temperatures by elimination of only $H_2$ and $N_2$ to yield pure and highly stoichiometric GaN thin films.

The following examples further illustrate the invention.

The synthesis reactions described hereinbelow were performed under prepurified nitrogen using standard Schlenk and drybox techniques. Dry, air-free solvents were distilled from sodium benzophenone ketyl prior to use. $^1H$ (300 MHz) NMR spectra were recorded on a Varian Gemini 300 and a Varian Unity 500 spectrometer and referenced to the solvent resonances ($C_6D_6$, $^1H$: δ7.15). FTIR spectra were recorded on a Nicolet Magna-IR 550 spectrometer either as a Nujol mull between KBr plates or in a 10 cm gas cell with KBr windows. Elemental analyses were performed by Desert Analytics (Tucson, Ariz.). Electron impact mass spectra were performed on a Finnigan-MAT Model 312 mass spectrometer (IE=70 eV, Source T=20° C.). Gallium trichloride (Aldrich, Milwaukee, Wis.) and trimethylchlorosilane (Aldrich) were used as received. $GaBr_3$ was prepared by the reaction of dry $Br_2$ and gallium metal and it was purified by sublimation. $SiMe_3N_3$ and $CH_3GaCl_2$ are available from Aldrich. Azidotrimethylsilane (Aldrich, 95%) was purified by distillation (50° C./175 mm) and its purity was checked by NMR and gas phase IR. $LiGaH_4$ was freshly prepared using literature methods (Shirk et al., Inorganic Synthesis 17:45–47). Trimethylsilane was prepared by reduction of trimethylchlorosilane with lithium aluminum hydride (Aldrich) which was recrystallized from diethyl ether prior to use. $LiN_3$ was prepared and its purity determined by powder diffraction and IR spectroscopy as described in Hoffman-Bang et al., Acta Chem. Scand. 11:581, 1957.

EXAMPLE 1

SYNTHESIS OF $HClGaN_3$

The synthesis of $HClGaN_3$ was accomplished via a metathesis reaction involving $HGaCl_2$ and $LiN_3$. $HGaCl_2$ was prepared according to the following reaction as described in Beachey et al., Inorg. Chem 19:783, 1990:

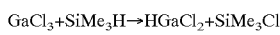

$GaCl_3 + SiMe_3H \rightarrow HGaCl_2 + SiMe_3Cl$

Interactions of this compound with rigorously dried $LiN_3$ at 20° C., followed by removal of the volatiles, results in a waxy solid which is readily crystallized in hexane to give a colorless solid in typically 85% yield based on the following reaction:

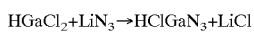

$HGaCl_2 + LiN_3 \rightarrow HClGaN_3 + LiCl$

Solid $LiN_3$ is added slowly through a solid addition funnel at 0° C. to a 30 mL benzene solution 1.58 g, 13.1 mmol containing $Cl_2GaH$. After stirring for 12 hours, the solvent is removed in vacuum to yield a waxy solid at 85% yield. This material is extracted several times with hexane and the combined filtrates are cooled at −5° C. to obtain a colorless crystalline solid. $HClGaN_3$ mp 70° C. dec. Anal. Calcd: C, 0.0; H, 0.68; N, 28.4; Cl, 24.0; Ga 47.02. Found: C, 0.20; H, 0.72; N, 28.06; Cl, 24.13; Ga 47.00. IR (Nujol): 2112 (vs $v_{as}N_3$) 1992 (s. $v_{as}Ga$—H), 1363 (m), 1303 (m), 1243 (m, $v_{sym}N_3$), 668 (w), 668 (w), 668 (w), 575 (vs, ρ Ga—H), 406 (m, υ Ga—N), 334 (m). EIMS (m/e): 443 [$(HClGaN_3)_3^+$-$H_2$], 408 [$(HClGaN_3)_3^+$-HCl], 402 [$(HClGaN_3)_3^+$-$HN_3$], 261 [$(HClGaN_3)_2^+$-HCl].

The elimination of LiCl is quantitative and its identity is readily established by powder X-ray diffraction. A complete elemental analysis for H, Cl, Ga and N content of the product indicated the formula $HClGaN_3$ and revealed lack of any measurable carbon impurities.

The X-ray crystallographic structure was determined as follows. Air and moisture sensitive crystals were loaded into a 0.3 mm capillary and sealed under nitrogen. A suitable specimen was mounted vertically in a Siemens P4 Autodiffractometer equipped with the LT-2a low temperature devices pre-set at −100° C. Centering of 25 randomly selected reflections between 15–30 2θ revealed a primitive tetragonal cell. Data collection of the ⅛ of the hemisphere gave 3432 reflections that merged to 1628 unique reflections. The small absorption profile was corrected using psi scan data collected at 10° intervals for four reflections with chi values near 90°. Solution by direct methods showed the asymmetric unit to be a cyclic tetramer of [HClGaN$_3$]$_4$ units with an alternating up-down Cl orientation. The intramolecular Ga—Ga distances ranged from 3.49 to 3.52 Å between azide bridged Ga atoms and from 4.87 to 4.90 between transannular Ga—Ga distances. The tetramer units formed extended zig-zag chains with an intermolecular Ga(3)—Ga(4) distance of 4.09 Å and a Ga(1)—Ga(2) distance of 4.18. These intermolecular Ga—Ga interactions are bridged by chlorine atoms with the intermolecular Ga—Cl distances ranging from 3.53 to 3.74 Å. Convergence led to final R/Rw 0.0660/0.0605. All data reduction, solution, and refinement calculations utilized the SHELTEXT Plus package of programs available from Siemens.

The X-ray crystallographic Lanalysis reveals that the compound in solid state consists of tetrameric [HClGaN$_3$]$_4$ units with a conformation as shown in FIG. 1 which is similar to cyclooctane. The X-ray crystallographic data is set forth in Table 1 and Table 2. The tetramer is formed by four Ga atoms bridged by the α-nitrogen of the azide groups, and the non-bridging positions are occupied by alternating up and down Cl atoms. Structures that contain Ga centers connected by the α-nitrogen of an azide group have been demonstrated for the polymeric chain (Me$_2$GaN$_3$)$_x$ as described in Atwood et al., J. Organomet. Chem. 394: C6, 1990 and for the Lewis acid-base adduct (H$_3$C)$_3$SiN$_3$GaCl$_3$ as described in Kouvetakis et al., Chem. of Mat. 1:476, 1989. Interestingly, the bis(dimethylamido) gallium azide, (Me$_2$N)$_2$GaN$_3$, was shown to consist of dimers formed by bridging dimethylamido (Me$_2$N) groups rather than azide ligands as described in Newmayer et al., J. Am. Chem. Soc. 117:5893, 1995.

Figure 2:
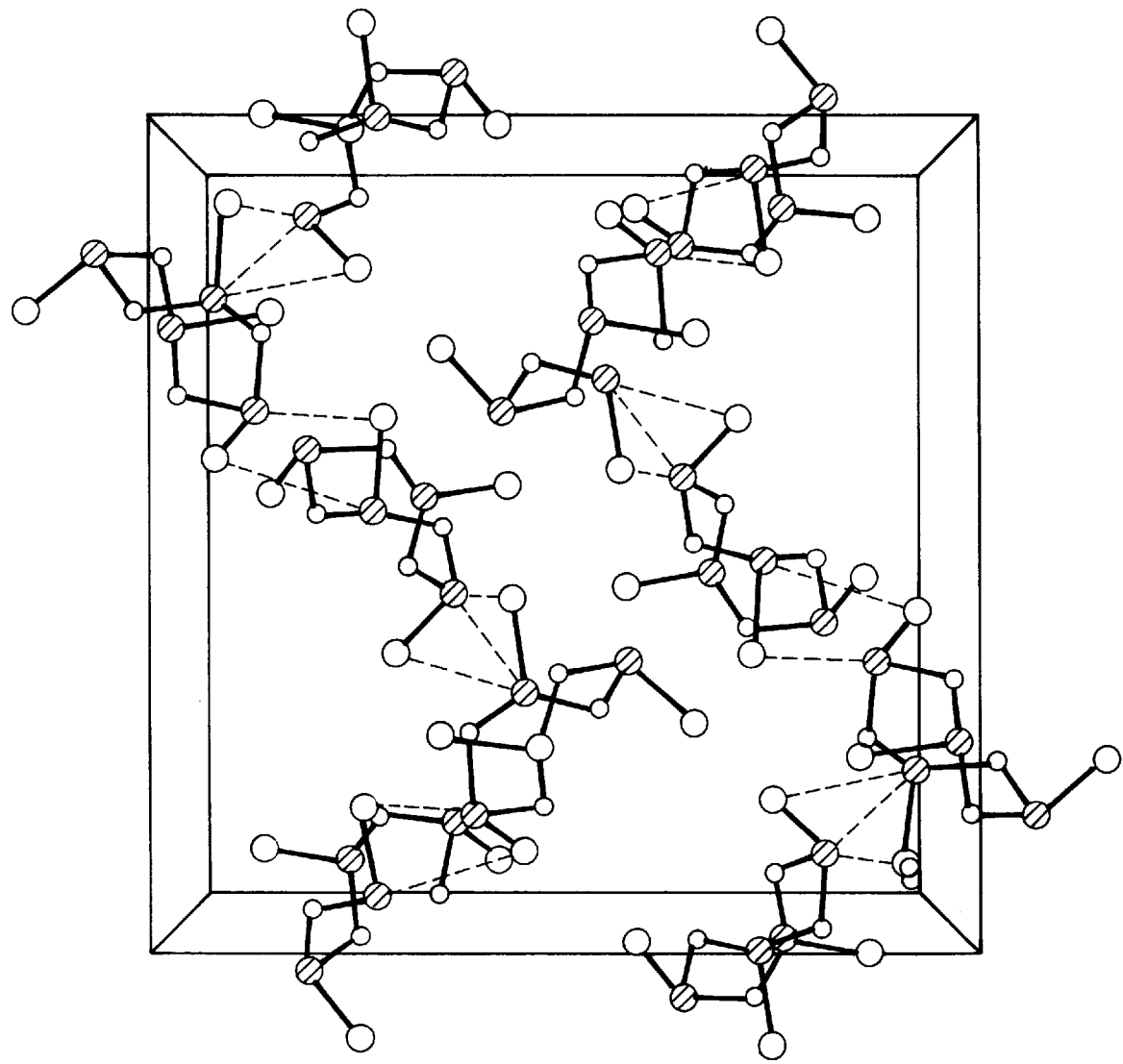
FIG. 2 is an illustration of a unit cell of azidochlorogallane.

HClGaN$_3$, however, is the first proven example of a Ga molecular ring system formed by means of bridged azides, although such structures have been suggested for the trimers [(C$_2$H$_5$)$_2$GaN$_3$]$_3$ and [(C$_2$H$_5$)$_2$AlN$_3$]$_3$ in solution by Muller et al., Z anorg. allg. Chem. 348:261, 1966; Muller et al., J. Organomet. Chem. 12:37, 1968. The Ga$_4$N$_4$ cyclic core of [HClGaN$_3$]$_4$ has intramolecular Ga—Ga distances, the distances between azide-bridged Ga atoms, ranging from 3.49 to 3.52 Å. The Ga—N and Ga—Cl distances vary from 1.918–2.063 Å and 2.134–2.183 Å, respectively. However, there are two distinct N—N bond distances, the shorter corresponding to the terminal N—N moiety of the azide group as can be seen from Table 1 and Table 2. This terminal bond is shorter by about 0.1 Å and it implies a considerably activated azide towards elimination of N$_2$. The tetramers form extended zig-zag chains via dative interactions between a terminal Cl atom and the neighboring Ga atom. A unit cell illustration is shown in FIG. 2. The intermolecular Ga—Cl distances range from 3.53–3.73 Å. As can be seen from FIG. 2, a notable feature of the long range structure is that only adjacent Ga atoms in the ring participate in the intermolecular interactions that are responsible for the formation of the chains.

The infrared spectra includes vibrations at 2115 cm$^{-1}$ $v_{as}$(N$_3$), 1990 cm$^{-1}$ $v_{as}$ (Ga—H), 1243 cm$^{-1}$ $v_s$(N3), 575 cm$^{-1}$ (Ga—H deformations), 406 cm$^{-1}$ $v_{as}$(Ga—Cl), and 334 cm$^{-1}$ (Ga—N—Ga bridging modes). The $^1$H NMR spectrum of the compound dissolved in toluene-d$_8$ at 20° C. consists of a broad peak at δ5.25, a shift characteristic of terminal Ga—H groups. The broadening is attributed to the quadiupolar Ga nuclei. This resonance becomes considerably sharper at −50° C. but the spectrum is otherwise unchanged. The mass spectra displayed isotopic envelopes for M$_3^+$-H as the highest mass peak at 443 amu (M=HClGaN$_3$) as well as mass peaks for (M$_3^+$-Cl), (M$_3^+$-N$_3$), M$_2^+$, and M$^+$. The calculated isostopic patterns are in excellent agreement with the experimental and support the proposed trimeric gas-phase structure.

TABLE 1

Selected Distances (Å) and Angles (deg) for (HClGaN$_3$)$_4$

Distances

| | | | |
|---|---|---|---|
| Ga(1)—Cl(1) | 2.134(11) | Ga(1)—N(1) | 2.063(16) |
| Ga(1)—N(10) | 1.951(14) | Ga(2)—Cl(2) | 2.184(5) |
| Ga(2)—N(1) | 1.918(17) | Ga(2)—N(4) | 1.970(15) |
| Ga(3)—N(3) | 2.183(9) | Ga(3)—N(4) | 1.994(15) |
| Ga(3)—N(7) | 1.951(17) | Ga(4)—Cl(4) | 2.178(5) |
| Ga(4)—N(7) | 1.987(14) | Ga(4)—N(10) | 2.023(16) |
| N(1)—N(2) | 1.233(19) | N(2)—N(3) | 1.127(22) |
| N(4)—N(5) | 1.236(19) | N(5)—N(6) | 1.132(21) |
| N(7)—N(8) | 1.254(19) | N(8)—N(9) | 1.150(21) |
| N(10)—N(11) | 1.257(19) | N(11)—N(12) | 1.115(21) |

Angles

| | | | |
|---|---|---|---|
| Cl(1)—Ga(1)N(1) | 100.4(5) | Cl(1)—Ga(1)—N(10) | 103.4(6) |
| N(1)—Ga(1)N(10) | 97.8(6) | Cl(2)—Ga(2)—N(1) | 103.8(5) |
| Cl(2)—Ga(2)N(4) | 100.1(4) | N(1)—Ga(2)—N(4) | 99.4(80 |
| Cl(3)—Ga(3)N(4) | 98.1(6) | Cl(3—Ga(3)—N(7) | 103.3(4) |
| N(4)—Ga(3)N(7) | 97.6(6) | Cl(4)—Ga(4)—N(70 | 98.7(5) |
| N(4)—Ga(4)N(10) | 98.4(5) | N(7)—Ga(4)—N(10) | 97.4(70 |
| Ga(1)—N(1)Ga(2) | 123.5(7) | Ga(1)—N(1)—N(2) | 115.0(12) |
| Ga(2)—N(1)N(2) | 120.8(13) | N(1)—N(2)—N(3) | 176.5(18) |
| Ga(2)—N(4)Ga(3) | 124.6(7) | Ga(2)—N(4)—N(5) | 116.7(11) |
| Ga(3)—N(4)N(5) | 118.7(11) | N(4)—N(5)—N(6) | 175.6(19) |
| Ga(3)—N(7)Ga(4) | 124.5(6) | Ga(3)—N(7)—N(8) | 118.4(11) |
| Ga(4)—N(7)—N(8) | 116.8(12) | N(7)—N(8)—N(9) | 178.1(20) |
| Ga(1)—N(10)—Ga(4) | 124.6(7) | Ga(1)—N(10)—N(11) | 119.7(11) |
| Ga(4)—N(10)—N(11) | 115.2(11) | N(10)—N(11)—N(12) | 178.9(20) |

TABLE 2

Crystal Data for(HClGaN$_3$)$_4$ at (−100° C.)

| | |
|---|---|
| space group: P4$_2$bc | mol wt = 148.2 |
| a = 17.920(3) Å | ρ$_{calcd}$ = 2.28 g cm$^3$ |
| c = 10.782(3) Å | μ$_{calcd}$ = 6.78 mm$^{-1}$ |
| V = 3462(2) Å$_3$ | size = 0.2 × 0.2 × 0.4 mm |
| Z = 8 | GOF = 1.96 | diffractometer: Siemens P$_4$
radiation: Mo K, = 0.17073 Å
monochromator: graphite crystal, 2θ = 12°
scan range, type: 3__ < 2θ < 50°
scan speed, width: variable 3–15.00°/min in ω
rflctns: 3432 total, 1628 independent, 1344((F) > 3σ(F))
R$_{int}$: 4%
final R indices: R = 0.0520; R$_w$ = 0.0564
all data: R = 0.0660; R$_w$ = 0.0605
$^a$R = Σ(||F$_o$| − |F$_c$||)/Σ|F$_o$|.
$^b$wR = [Σw(|F$_o$|$^2$ − |F$_c$|$^2$)$^2$/Σw(F$_o$)$^2$]$^{1/2}$.

EXAMPLE 2

SYNTHESIS OF H$_2$GaN$_3$ BY METATHESIS USING H$_2$GaCl

This preparation of H$_2$GaN$_3$ utilized the interaction of freshly prepared H$_2$GaCl as described in Goode et al., J. Chem. Soc. Chem. Commun. 768, 1988 with LiN$_3$ to yield a colorless liquid and a stoichiometric amount of LiCl as shown by the following reaction:

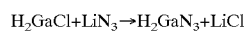

H$_2$GaCl+LiN$_3$→H$_2$GaN$_3$+LiCl

Figure 3:
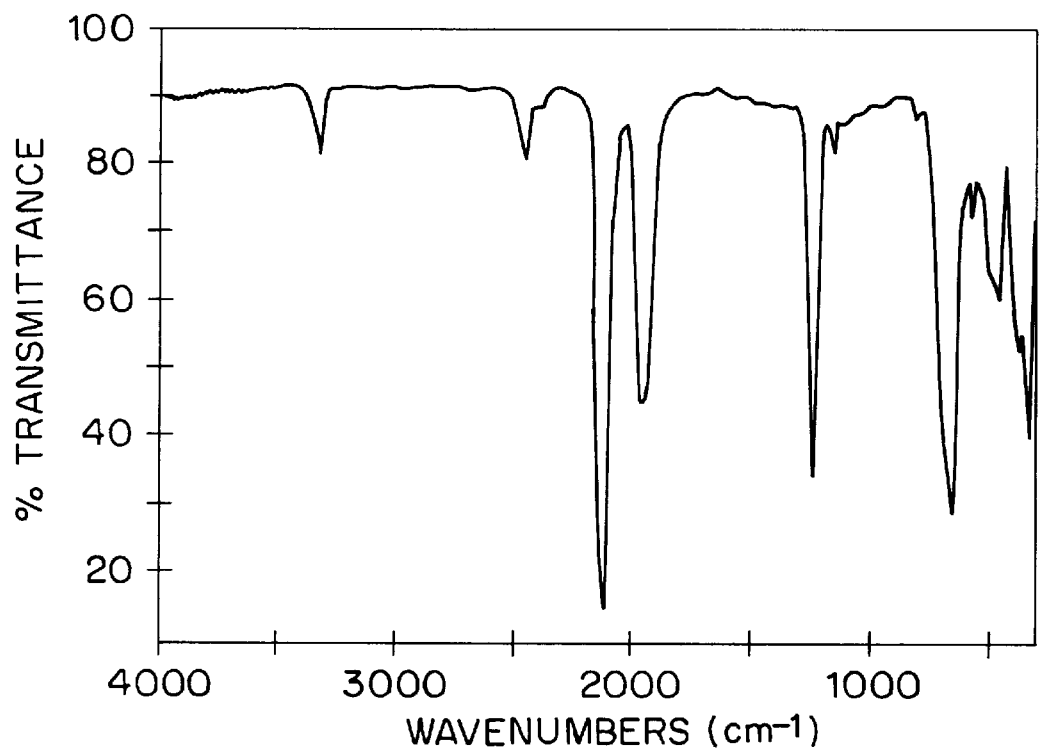
FIG. 3 is the infrared spectrum of $(H_2GaN_3)_n$.
Figure 4:
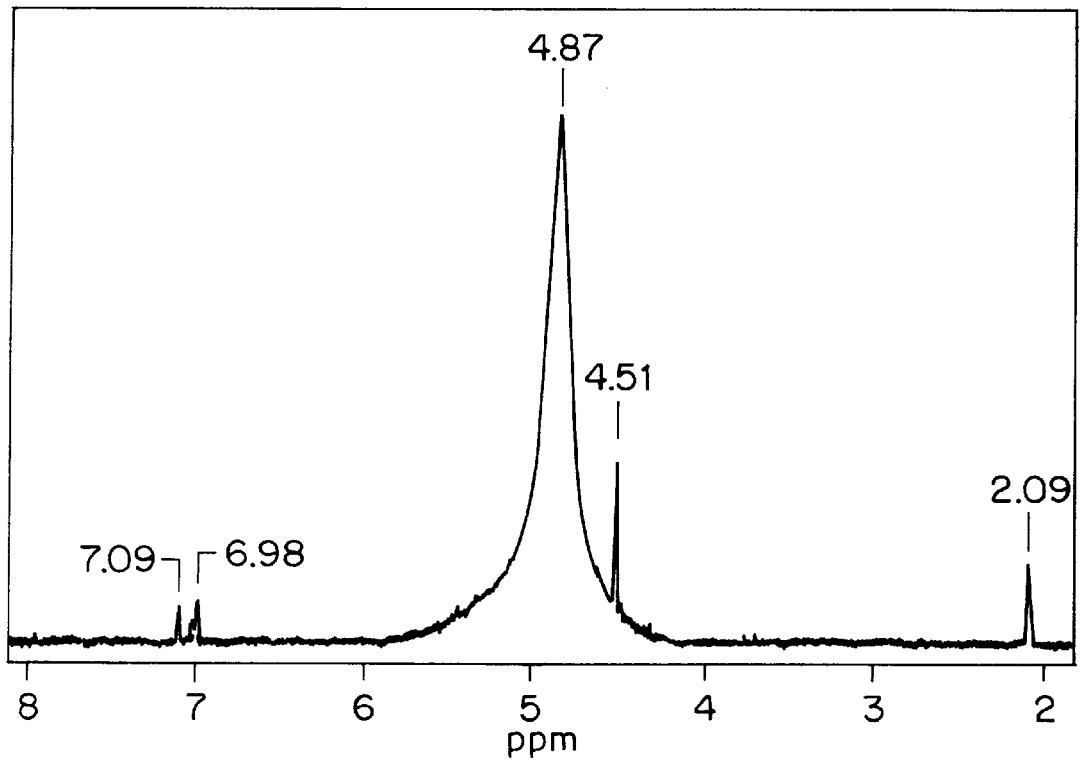
FIG. 4 is the $^1H$ NMR spectrum of $(H_2GaN_3)_n$ dissolved in toluene-$d_8$ at 20° C.

A solution of H$_2$GaCl (0.435 g, 4.06 mmol) in benzene (25 mL) was added to a suspension of LiN$_3$ (0.260 g, 5.31 mmol) in toluene (20 mL). The mixture was stirred at ambient temperature for 3 hours during which time the suspension turned light gray. The mixture was then filtered and the solvent was removed in vacuum to yield a clear slightly viscous liquid. The filtrate (0.183 g) was readily identified as LiCl by powder X-ray diffraction. The product isolated in this fashion is stable at −30° C. and minor decomposition is observed at room temperature. It is extremely difficult to collect and any attempt to transfer the pure product from the reaction flask using a metal or glass spatula caused instant decomposition often accompanied with spontaneous ignition. The remaining residue is always crystalline GaN free of Cl or any other impurities. The sample used for CVD experiments was first dissolved in benzene and then transferred to the appropriate container. The solvent was removed in the vacuum line and the sample was attached to the vacuum chamber. The gaseous precursor was transported into the reactor under vacuum through a leak valve. It is important to note that high quality $H_2GaCl$ must be used to synthesize $H_2GaN_3$. Halide contaminations such as $HGaCl_2$ in the starting material yielded impure products which were then treated with $LiGaH_4$ to remove the chloride impurity. Filtration gave a clear solution of $H_2GaN_3$ in toluene. Neat $H_2GaN_3$ is unstable in contact with sharp objects. It decomposes with release of heat and often ignites spontaneously. It should be handled with extreme care in solvents. The infared spectrum is shown in FIG. 3. The NMR spectrum is shown in FIG. 4. IR: 3360 (w, $v_{as}N_3+v_{sym}N_3$), 2470 (w, $2\times v_{as}N_3$), 2130 (vs $v_{as}N_3$) 1980 (s. $v_{as}GA$—H) 1240 ($v_{sym}N_3$), 672 (s, Ga—H) scissoring, twisting, wagging), 587 (m, ρ_Ga—H), 479 (m, v_Ga—N), 345 (m, δ_M—N—M). $^1H$ NMR: for 20° C. δ4.87 (broad singlet, Ga—H), for −50° C. δ4.81 (s, Ga—H); 4.71, (shoulder Ga—H). (The combination band at 3360 cm$^{-1}$ should not be confused with an N—H stretch. There was no obervation of N—H type vibrational modes in the IR or N—H resonances in the NMR). EIMS (m/e):, 340 [$(H_2GaN_3)_3^+$-$H_2$], 300 [$(H_2GaN_3)_3^+$-$N_3$], 227 [$(H_2GaN_3)_2^+$-H], 186 [$(H_2GaN_3)_2^+$-$N_3$], 114 $(H_2GaN_3)^+$.

The IR spectrum of the product displays two distinct and very intense bands at 2130 cm$^{-1}$ and 1980 cm$^{-1}$ assigned $v_{as}N_3$ and $v_{as}Ga$—H respectively. Other notable features include $v_{sym}N_3$ at 1238 cm$^{-1}$, v(Ga—N) at 475 cm$^{-1}$, v(N—Ga—N) at 345 cm-1 and a strong absorption at 710–675 cm$^{-1}$ corresponding to $GaH_2$ scissoring deformations (FIG. 3). The latter is very prominent in molecules containing terminal Ga—$H_2$ units such as $(H_2GaCl)_2$, as described in Goode et al., J. Chem. Soc. Chem. Commun. 768, 1988 and $(Me_2NGaH_2)_2$ as described in Baxter et al., Chem. Soc. Dalton, Trans. 807, 1985; Harrison et al., Chem. Soc. Dalton 1554, 1972, but it is not observed in the spectrum of $(HClGaN_3)_4$. The weak bands at 3360 cm$^{-1}$ and 2470 cm$^{-1}$, as visible in FIG. 3, are overtones and correspond to $v_{as}N_3+v_{sym}N_3$ and $2\times v_{sym}N_3$ respectively. These features are common for organometallic azides of Al, Ga, and In and have been previously observed in the IR spectra of $X_2MN_3$, (X=Cl, Br, I), and M=Al and Ga. as described in Muller et al., J. Organomet. Chem. 12:37, 1968; Dechnicke et al., Z. anorg. allg. Chem. 444:71, 1978.

The $^1H$ NMR spectrum at 20° C. in toluene-$d_8$ revealed a rather broad Ga—H resonance at δ4.87, a value significantly different than that found for $(HClGaN_3)_4$ (δ5.25) and for $H_2GaCl$ (δ5.40) as reported in Goode et al., J. Chem. Soc. Chem. Commun. 768, 1988. The peak sharpens considerably at −50° C. but its position remains the same. After several hours, at room temperature an additional sharp peak was observed at δ4.51 and was accompanied by formation of a very small amount of a white precipitate (FIG. 4). This feature at δ4.51 has been previously attributed to dissolved $H_2$ and its presence suggests minor decomposition with loss of hydrogen as previously reported in Wells et al., Inorg. Chem. 36:4135, 1997. In contrast, the $^1H$ NMR spectrum in THF-$d_8$ shows a single, relatively sharp, resonance at δ4.86, and does not indicate any dissolved $H_2$ or precipitate formation for solutions that remained at room temperature for several days, indicating that a THF complex of the compound may be responsible for the remarkable stability of $H_2GaN_3$ over time. The mass spectrum displays the calculated isotopic patterns for the ions $(H_2GaN_3)^+$ at 114 amu, [$(H_2GaN_3)_2^+$-H] at 227 amu, [$Ga_3N_9$] at 334, and [$(H_2GaN_3)_3^+$-$H_2$] at 340 amu.

EXAMPLE 3

SYNTHESIS OF $Br_2GaN_3$, and REDUCTION TO FORM $H_2GaN_3$, and $D_2GaN_3$ $Br_2GaN_3$ is prepared from the Lewis acid-base adduct $SiMe_3N_3.GaBr_3$, a crystalline solid that is stable at room temperature but decomposes thermally via elimination of one mole of $SiMe_3Br$ at T>50° C. to yield 3 as a colorless polymeric solid. The synthetic procedure is summarized as follows:

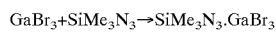

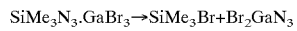

HBrGaN$_3$, $H_2GaN_3$, and $D_2GaN_3$ are prepared via reduction of $Br_2GaN_3$ with an excess of $LiGaH_4$ and $LiGaD_4$ respectively as follows:

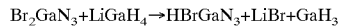

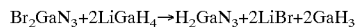

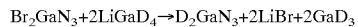

Formation of stable complexes between the Lewis base $SiMe_3N_3$ and Lewis acids $GaCl_3$, $SnCl_4$, and $BBr_3$ have been previously demonstrated by Kouvetakis et al., Inorg. Chem. 36:1792, 1997; Thayer et al., Inorg. Chem. 4:114, 1965. In the case of $SiMe_3N_3.GaCl_3$, a structural characterization showed a bridging Ga—N—Si azide linkage rather than a Ga—N—N—N—Si linkage as reported in Kouvetakis et al., Inorg. Chem. 36:1792, 1997. The $SiMe_3N_3.GaBr_3$ compound was readily obtained by a combination of freshly sublimed $GaBr_3$ with $SiMe_3N_3$ and crystallized in toluene to give colorless needle-shaped crystals as follows.

To a suspension of $GaBr_3$(5.0 g, 16.12 mmol) in hexane, was added $SiMe_3N_3$ (2.15 ml, 16.20 mmol) by syringe at room temperature. The mixture was stirred until all the material dissolved and a clear solution was obtained. Concentration and cooling of the solution yielded 6.65 g (95%) of 4 as colorless needles; m.p. 38° C. $^1H$ NMR: δ0.64 (singlet, CDCl$_3$). IR (nujol): 3343 (w), 2404 (m), 2173 (vs), 1421 (w), 1263 (s), 1208 (s), 1100 (w), 860 (vs), 789, 768, 755 (s), 638(w), 556 (w), 480 (m), 347 (m). Anal. calcd.: Ga: 16.47, Br: 56.47; Found: Ga: 16.17, Br: 54.98.

Figure 5:
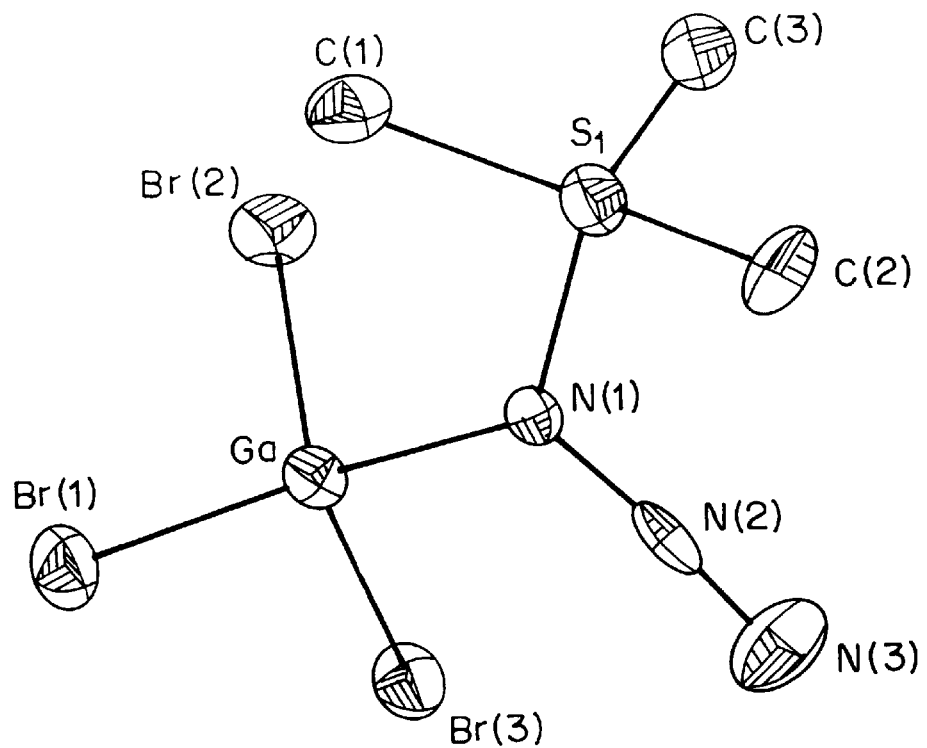
FIG. 5 is an illustration of the molecular structure of $SiMe_3N_3 \cdot GaBr_3$.

A suitable specimen was loaded into a 0.3 mm X-ray capillary and sealed under nitrogen. The capillary was mounted vertically in a Siemens P4 Autodiffractometer equipped with a LT-2a low-temperature device pre-set at −100° C. Centering of 25 randomly selected reflections between 15–30 2θ revealed a primitive orthorhombic cell. Data collection gave 1701 reflections that merged to 1159 unique reflections. The data were corrected for absorption by use of psi scan data collected at 10° intervals for four reflections with chi values near 90°. Solution by direct methods showed the asymmetric unit to be independent $SiMe_3N_3$—$GaBr_3$ molecules. The closest intermolecular distance is 3.82 Å between Br(1) and N(3). The Br(3) atom is 3.14 from the position of the H(1a) atom [riding on C(1)]. The X-ray crystallographic analysis summarized in Tables 3 and 4 reveal that the molecule has a geometry similar to that of $SiMe_3N_3 \cdot GaCl_3$ and consists of monomeric units containing a Ga—N—Si linkage as shown in FIG. 5. Interestingly, the Si—C bond (1.804 Å) is significantly shorter than expected for a single bond, and the Ga—N bond distance (2.022 Å) is very close to the Ga—N distances found for the $(Me_3GaN_3)_x$ polymer in which the Ga atoms are linked together by the α-nitrogens of the azide group to form an one-dimensional polymeric chain. There are two distinct N—N distances in the azide group, with the shorter one corresponding to the terminal N—N bond (1.129 Å), a feature which is common among gallium compounds with bridging azides. Spectroscopic characterizations by IR and NMR and elemental analysis are consistent with the molecular formula derived from the X-ray structure. The compound decomposes in the mass spectrometer to give $SiMe_3Br$ and $Br_2GaN_3$ species.

TABLE 3

Structure determination summary

| | | | |
|---|---|---|---|
| chemical formula | $C_3H_9Br_3GaN_3Si$ | formula weight | 424.7 |
| crystal system | orthorhombic | space group | $Pna2_1$ |
| a (Å) | 14.907(5) | T (K) | 173 |
| b (Å) | 7.759(3) | λ (Mo Kα, Å) | 0.71073 |
| c (Å) | 10.789(5) | $\rho_{calc}$ (gcm$^{-3}$) | 2.26 |
| V (Å$^3$) | 1248(1) | μ (mm$^{-1}$) | 11.86 |
| Z | 4 | wR (%) | 4.05 |
| | | R (%) | 5.06 |

$aR = \Sigma\|F_o\| - |F_c\|/\Sigma|F_o|$, $bR[\Sigma w(|F_o| - |F_c|)^2/\Sigma w(|F_o|^2]^{1/2}$, $w = 1/\sigma^2(|F_o|)$

TABLE 4

Selected bond distances (Å) and angles (deg.)

| | | | |
|---|---|---|---|
| Ga—N1 | 2.022(15) | N2—N3 | 1.129(20) |
| Si—N1 | 1.826(13) | Si—C1 | 1.804(19) |
| Ga—Br1 | 2.300(19) | Si—C2 | 1.807(19) |
| N1—N2 | 1.267(18) | Si—C3 | 1.810(26) |
| Br1—Ga—Br2 | 113.7(3) | Ga—N1—Si | 129.8(6) |
| C1—Si—C2 | 115.0(11) | Ga—N1—N2 | 115.2(10) |
| C2—Si—C3 | 113.7(9) | N2—N1—S1 | 115.0(5) |
| C1—Si—C3 | 112.6(9) | Br2—Ga—N1 | 103.7(6) |
| N1—Si—C1 | 106.4(8) | Br1—Ga—Br3 | 112.9(9) |
| N1—N2—N3 | 176.2(19) | Br1—Ga—N1 | 107.0(8) |

A sample of the previously synthesized $SiMe_3N_3 \cdot GaBr_3$ (2.4 g, 5.66 mmol) was heated at 50–70° C. under vacuum for 4 hours to yield a compound 2 (1.5 g, 5.52 mmol, 97%) as a colorless solid and a volatile liquid that was collected at −196° C. and was identified as $SiMe_3Br$ (0.86 g, 5.623 mmol) by gas phase IR. Compound 2: m.p. 250° C. EIMS m/e: shows isotopic envelopes centered at 773 $(M^+)_3$—$N_3$, 734 $(M^+)_3$—Br, 501 $(M^+)_2$—$N_3$, 229 $(M^+)$—$N_3$; IR (nujol): 3343 (w, $v_{as}N_3+v_{as}N_3$), 2394 (m, $2v_sN_3$), 2170, (vs, $v_{as}N_3$), 1197 (s, $v_sN_3$), 1096 (w, comb. band), 734 (s, δ $N_3$), 548 (m, γ N3), 452 (s, $v_{as}$Ga—N), 343 (s, δ NgaN).

Heating $SiMe_3N_3 \cdot GaBr_3$ under vacuum at about 50° C. eliminated $SiMe_3Br$ quantitatively and resulted in the formation of $Br_2GaN_3$ as a finely divided colorless solid. The IR spectrum of the material is identical to the product of the reaction of $I_2GaN_3$ with liquid $Br_2$ as reported by Wiberg Von et al., Z. Annorg. allg. Chem. 394:197, 1972. Mass spectrometric analysis of the $Br_2GaN_3$ compound obtained by direct vaporization of the sample into the spectrometer at 70° C. reveals the highest mass peak at 773 amu which corresponds to $[(Br_2GaN_3)_3\text{-}N_3]^+$. This is consistent with the vapor containing trimeric $(Br_2GaN_3)_3$ units. On the other hand, higher intensity peaks at 502 amu and 229 amu, corresponding to $[(Br_2GaN_3)_2\text{-}N_3]^+$ and $[(Br_2GaN_3)\text{-}N_3]^+$ respectively, suggest that the presence of dimers and monomers is also possible, although these species could have been generated through the cleavage of the parent ion.

The synthesis of $HBrGaN_3$ was accomplished by the interaction of $Br_2GaN_3$ with an equivalent of $LiGaH_4$ in $C_6H_6$.

$HBrGaN_3$ was synthesized as follows: To a suspension of $Br_2GaN_3$ (3) (1.0 g, 3.67 mmol) in benzene, $LiGaH_4$ (0.297 g, 3.67 mmol) was added by a solid addition funnel at 5° C. The mixture was stirred for 4 hours at room temperature during which time a gray precipitate formed. The mixture was filtered and the solvent was removed in vacuum to yield a viscous colorless oil (0.56, 2.93 mmol, 80% yield). IR: 3337 (w), 2415 (w), 2148 (vs), 1996 (m), 1206 (s), 1106(sh), 758(m), 674(vw), 580 (vs), 410 (vs), 326(s). $^1H$ NMR (toluene-d$_8$): $\delta_{13}$ 5.093 at 20° C. and δ4.98 at −50° C. Anal. calcd. C: 0.0, H: 0.52, N: 21.76, Br: 41.45. Found C: 0.4, H: 0.87, Br: 40.61 N, 18.5 (the instability of the compound towards GaN formation (a refractory) at almost 70° C. prevents determination of exact N analysis). EIMS(m/e): isotopic envelopes centered at 578 $(M^+)_3$, 535 $(M^+)_3$—$N_3$, 498 $(M^+)_3$—Br, 457 $(M^+)_3$—$N_3$—Br, 418 $(M^+)_3$—$Br_2$, 344 $(M^+)_2$—$N_3$. The precipitate was identified as LiBr by powder X-Ray diffraction. The product was isolated as a clear and slightly viscous liquid after filtration from the insoluble byproducts, which consist of crystalline LiBr and a gray material that presumably resulted from the decomposition of $GaH_3$. Elemental analysis of the product indicated the formula as $HBrGaN_3$ and revealed a lack of significant carbon impurities. The infrared spectrum is very simple and includes vibrations at 2148 cm$^{-1}$ [$v_{13\ as}N_3$], 1995 [$v_{as}$Ga—H], and a strong band at 580 cm$^{-1}$ corresponding to Ga—H deformations. The $^1H$ NMR spectrum in d$_8$ toluene at 20° C. contains a broad peak at δ5.093, upfield from that of δ5.25 in the spectrum of $HClGaN_3$, a shift characteristic of terminal Ga—H groups. The mass spectrum obtained by direct vaporization of the compound at 20° C. displays isotopic bands for $(M_3^+\text{-}H)$, $[M_3=(HBrGaN_3)_3]$ at 578 amu, $(M_3^+\text{-}N_3)$, $(M_3^+\text{-}Br)$, and $(M_2^+\text{-}Br)$. The observed patterns are in good agreement with the calculated patterns.

$H_2GaN_3$ was synthesized as follows: To a suspension of $LiGaH_4$ (0.750 g, 9.25 mmol) in benzene, 3 (1.0 g, 3.67 mmol) was added at 5° C. by a solid addition funnel. The mixture was stirred at 20° C. for 3–4 hours during which time the suspension became light gray. The mixture was then filtered and the solvent was removed in vacuum to yield $H_2GaN_3$ as a clear viscous liquid. Bp: 40° C., 0.20 Torr. IR: 3344(w), 2465(w), 2130(vs), 1970(s), 1240(s), 661(s), 578 (vw), 466(m), 343(m). (IR gas phase, see Table 5). $^1H$ NMR (toluene-d$_8$): δ4.86 at 22° C. and δ4.81 at −50° C. Anal. calcd: C: 0.0, H: 1.75, N: 36.84: Found: C 0.34, H: 1.59, N: 35.67. EIMS (m/e): isotopic envelopes centered at 340 $(M^+)_3$—$H_2$, 299 $(M^+)_3$—$H_2$—$N_3$, 227 $(M^+)_2$—H, 186 $(M^+)_2$—$N_3$—114 $(M^+)$.

Figure 6:
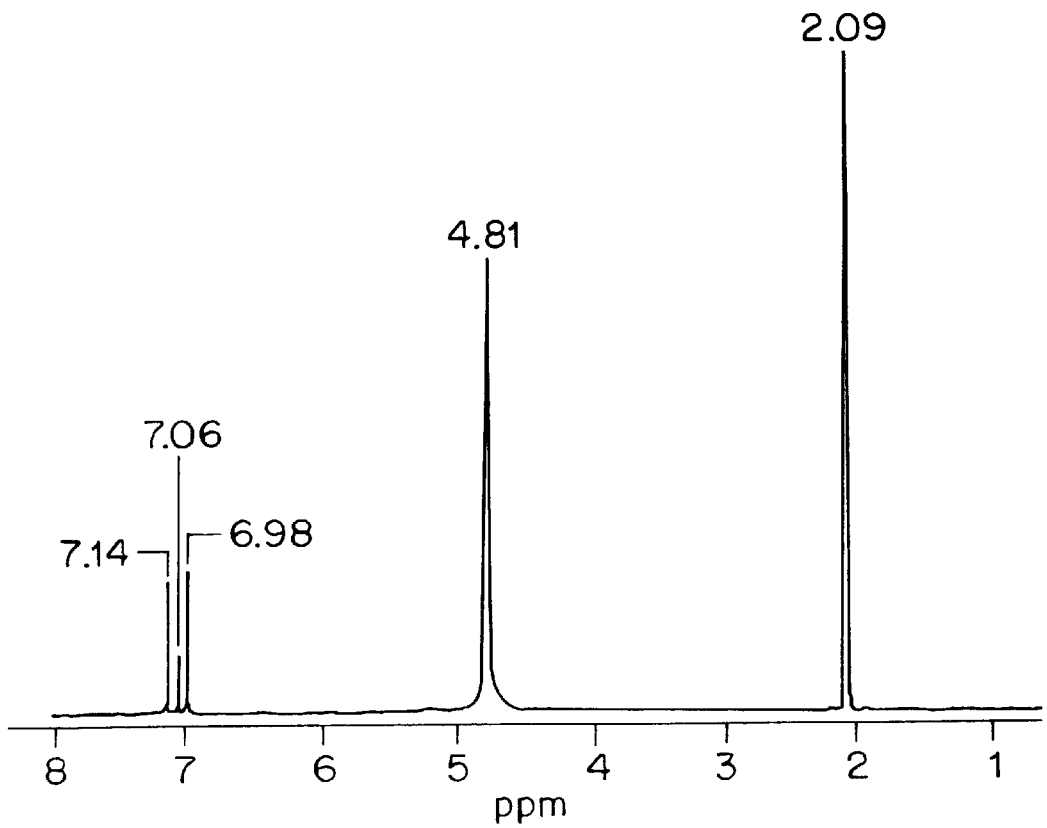
FIG. 6 is the $^1H$ NMR spectrum of $H_2GaN_3$ at –50° C. dissolved in $d_8$ toluene.

The reaction of $Br_2GaN_3$ with two equivalents of $LiGaH_4$ followed by filtration and removal of the solvent yielded as a clear viscous liquid that decomposes rapidly upon exposure to air. The IR (thin liquid film) and NMR spectra of the compound are essentially identical to those obtained from the product of the reaction of $H_2GaCl$ with $LiN_3$ as reported by McMurran et al., J. Am. Chem. Soc. 120: 5233, 1998. The low-temperature $^1H$-NMR spectrum obtained in d$_8$ toluene at −50° C. displays a very sharp peak at δ4.81, that is substantially different than the value obtained for $HBrGaN_3$. FIG. 6 illustrates a representative low temperature $^1H$ NMR spectrum of a sample that was kept at room temperature for five days after preparation. The spectrum shows that the compound is reasonably pure and indicates good stability over time. The mass spectrum of the compound that was obtained by direct vaporization confirms that the compound is pure and free of any halide contamination. The highest mass peak was observed at 341 amu which corresponds to the mass of $(H_2GaN_3)_3{}^+$-H. Trap-to-trap distillation from room temperature into a series of traps held at 0° C., −15° C., and −196° C. resulted in a collection of the pure sample at the −15° C. trap. The distillation experiments demonstrate that the compound is quite volatile at 20° C. and also has a significant vapor pressure at room temperature. This kind of volatility is a crucial factor for its application as a practical CVD precursor. The compound was conveniently purified by reduced-pressure distillation to give a colorless liquid (bp 40° C., 0.200 torr). Elemental analysis of the purified product is consistent with the $H_2GaN_3$ formula and revealed no measurable carbon impurities.

Figure 7:
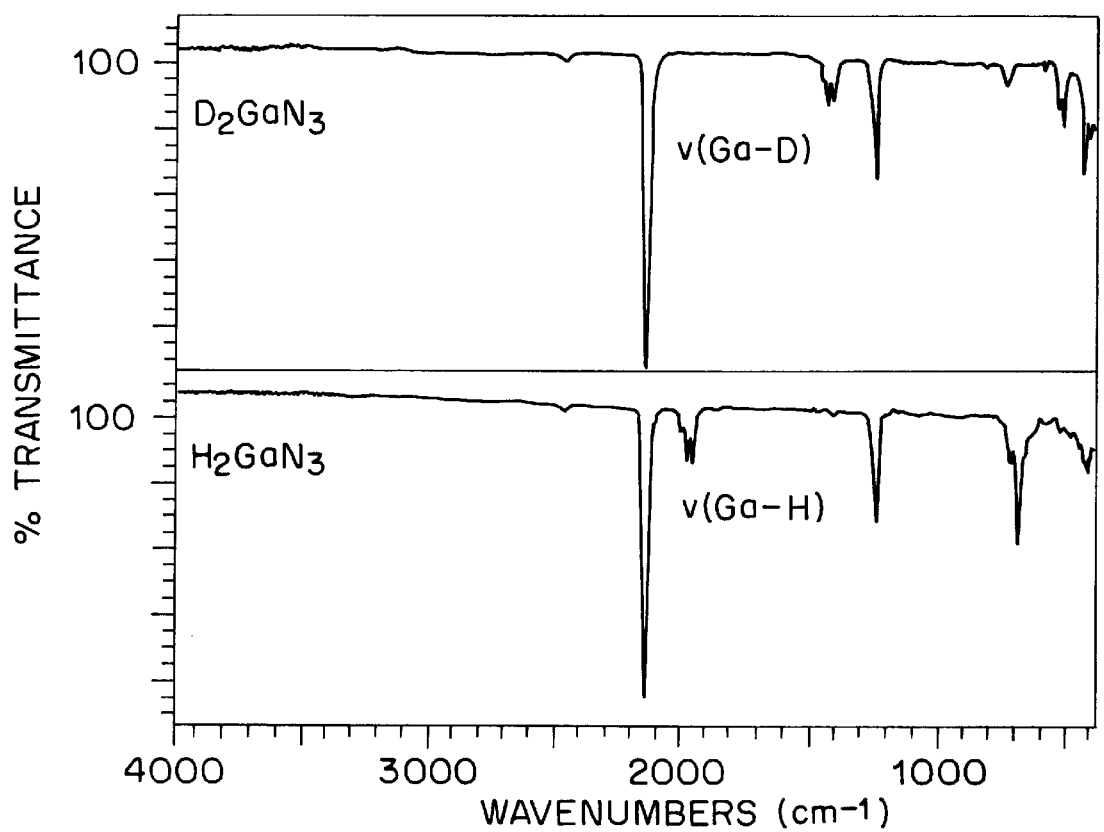
FIG. 7 is the FTIR gas phase spectra of $D_2GaN_3$ and $H_2GaN_3$.

$D_2GaN_3$ was synthesized as follows. To a suspension of $Br_2GaN_3$ (1.0 g, 3.67 mmol) in 25 mL of $C_6H_6$ was added (0.77 g, 9.2 mmol) of $LiGaD_4$ by solid addition funnel at 5° C. The mixture was stirred at room temperature for 5 hours during which time the suspension became gray. The mixture was then filtered and the solvent in the filtrate was removed in vacuum to yield the product as a clear liquid (0.350 g, 83%). Bp: 40° C., 0.20 Torr. IR(thin film): 3340(w), 2470 (w), 2120(vs), 1426(s),1400(s), 1235(s), 728(s), 680(w), 504(m), 390(m). (IR gas phase, see Table 5). EIMS (m/e): isotopic envelopes centered at 345 $(M^+)_3$—D, 305 $(M^+)_3$—$N_3$, 230 $(M^+)_2$ 190 $(M^+)_2$—$N_3$. The perdeuterated azidogallane was obtained from the reaction of an excess of $LiGaD_4$ with $Br_2GaN_3$ and was readily distilled at a reduced pressure (bp 40° C., 0.20 Torr) to give a viscous liquid which is thermally more stable than the isotopically normal analog. The compound was characterized by its IR (liquid thin film and gas phase) and mass spectra and its identity was confirmed by elemental analysis. The mass spectrum revealed a prominent isotopic envelope for $[D_2GaN_3]_3{}^+$-D at 345 amu which was in excellent agreement with the calculated pattern, and its fragmentation pattern was consistent with a trimeric structure. Particularly instructive is the simplicity of the gas phase IR spectrum of $D_2GaN_3$, which was obtained at 25° C. in a 10 cm cell fitted with KBr windows. It is compared in FIG. 7 to the corresponding spectrum of $H_2GaN_3$ which was recorded at nearly identical conditions. The main point is that the absorptions near 1950–2000 cm$^{-1}$ and 680–725 cm$^{-1}$ representing the stretching and bending modes of terminal Ga—H bonds respectively, have shifted to 1400–1450 cm$^{-1}$ and 500–502 cm$^{-1}$, respectively, for the perdeuterated compound. The energy shifts induced by the deuteration are remarkably close to the calculated values and provides further evidence for the identification of the $H_2GaN_3$ molecule. The frequencies of the azide absorptions at 2145 cm$^{-1}$ and 1232 cm$^{-1}$ corresponding to antisymmetric and symmetric stretching vibrations, respectively, remain unchanged. Furthermore, the IR spectra revealed multiple Ga—H and Ga—D bands at (1997, 1973, 1950) cm$^{-1}$ and (1425, 1400) cm$^{-1}$ respectively. Interestingly a similar splitting pattern was observed for ν(Ga—H) in the IR spectra of $Ga_2H_6$ vapor and was attributed to unresolved P and R branches in this highly symmetric compound in accordance with Pulham et al., J. Am Chem. Soc. 113:5149–5162, 1991; Goode et al., J. Am Chem. Soc. 111:1936–1937, 1989. In this case, the presence of cyclic $[(D_2)H_2GaN_3]_2$ dimers and $[(D_2)H_2GaN_3]_3$ trimers in the gas phase samples cannot be ruled out and a mixture of these could give rise to the IR bands in the Ga—H and Ga—D stretching regions of the spectrum. High resolution spectra obtained by standard techniques are able to derive precise structural information of this very simple molecular system.

TABLE 5

Gas IR Spectra of $H_2GaN_3$ and $D_2GaN_3$ (350–4000 cm$^{-1}$) at 25° C.

| $H_2GaN_3$ | | $D_2GaN_3$ | | |
|---|---|---|---|---|
| ν/cm$^{-1}$ | intensity | ν/cm$^{-1}$ | intensity | assignment* |
| 2462 | vw | 2462 | vw | 2 × 1231 |
| 2144 | vs | 2140 | vs | asym ν($N_3$) |
| 1995 | w | 1445 | w | ν(Ga—H)$A_1$ |
| 1973 | m | 1426 | m | ν(Ga—h)E |
| 1950 | m | 1399 | m | ν(Ga—h)E |
| 1231 | s | 1234 | m | sym ν($N_3$) |
| | | 730 | vw | δ($N_3$) |
| 724 | m | 530 | m | (H—Ga—H)E bending |
| 685 | s | 502 | s | (H—Ga—H)$A_1$ bending |

*The peak assigmnent for the Ga—H modes is based on the trimeric $(H_2GaN_3)_3$ ring structure with $C_{3v}$ symmetry.

EXAMPLE 4

SYNTHESIS OF $HCH_3GaN_3$ $CH_3ClGaN_3$ is prepared as follows:

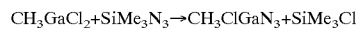

and characterized by X-ray diffraction, elemental analysis, mass spectra and NMR. Reduction of $CH_3ClGaN_3$ with $LiGaH_4$ results in formation of $HCH_3GaN_3$ according to the following reaction:

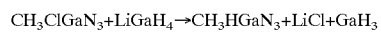

It is a volatile liquid having a boiling point at 50° C. and 0.20 torr and is readily distilled and purified without decomposition.

EXAMPLE 5

NORMAL MODE ANALYSIS AND AB INITIO CALCULATIONS OF $[H_2GaN_3]_2$, $D_{2H}$ AND $[H_2GaN_3]_3$, $C_{3V}$

The observation of multiple bands in the Ga—H stretching region of the IR spectra prompted a qualitative normal mode analysis for the possible dimeric $[H_2GaN_3]_2$ and the trimeric $[H_2GaN_3]_3$ forms of compound $H_2GaN_3$. The same theoretical treatment of $H_2GaN_3$ applies to $D_2GaN_3$. ab initio computations of related but simpler model compounds were also performed, which aid in the actual assignment of the observed spectra.

Figure 8:
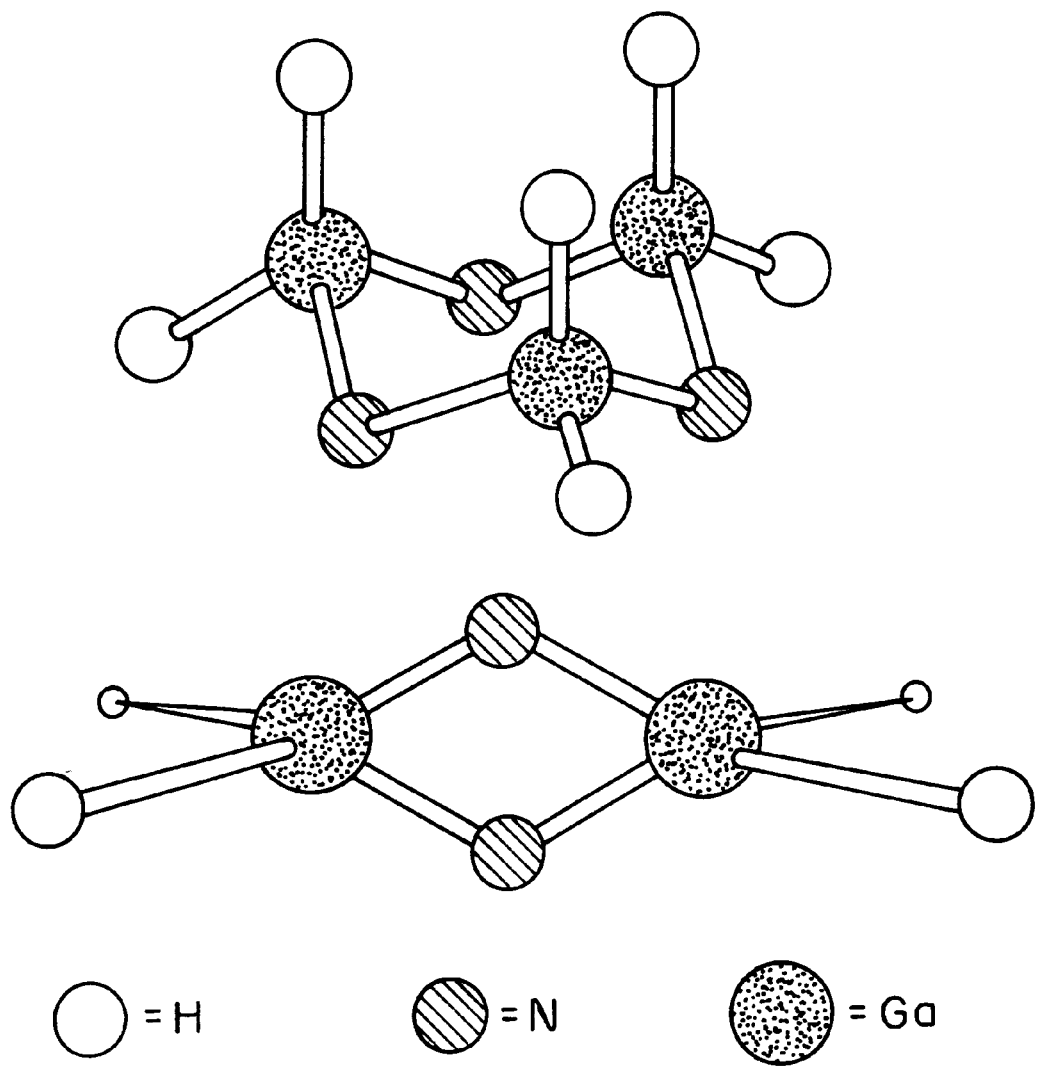
FIG. 8 is an illustration of dimer $(H_2GaN_3)_2$ and trimer $(H_2GaN_3)_3$.

The dimer $[H_2GaN_3]_2$ has a $D_{2h}$ structure in which the terminal $GaH_2$ groups are in one plane and the two bridging azides groups are perpendicular to this plane, as illustrated in FIG. 8. The normal mode analysis may be restricted to the Ga—H bond stretching and the H—Ga—H bond bending to facilitate assignment of the observed peaks attributable to the corresponding stretching and bending modes. Group theoretical analysis of the Ga—H terminals bonds reveals that they correlate into $A_g+B_{3g}+B_{1u}+B_{2u}$ irreducible representations in the $D_{2h}$ group. On the other hand, the H—Ga—H bond angles correlate into $A_g+B_{2u}$ modes. Among the four stretching modes, which correspond to the Ga—H stretches for the dimer, only the $B_{1u}$ and $B_{2u}$ modes are IR-active on the basis of dipole selection rules. Thus, only two IR stretching bands should be observed for the dimer.

The trimeric species $[H_2GaN_3]_3$ also shown in FIG. 8 has an equilibrium chair conformation and a $C_{3v}$ symmetry. The normal mode analysis was again restricted to the Ga—H stretching and H—G—H bending modes. The six Ga—H bonds of the trimer correlate in the $C_{3v}$ group into two $A_1$+two E normal stretching modes all of which are IR and Raman active in the $C_{3v}$ symmetry. The H—G—H bond angles correlate into $A_1$+E bending normal modes which are IR active.

In order to gain quantitative insight into the vibrational frequencies of the various modes, ab initio computations using MØller-Plesset second and fourth order perturbation (MP2 and MP4) computations were performed. Relativistic effective core potentials (RECPs) were employed for the Ga atom that retained the outer $4s^24p^1$ shells in the valence space replacing the remaining electrons with RECPs. These RECPs were used in conjunction with valence Gaussian (3s3p1d) basis sets for Ga and [5s1p/3s1p] basis sets for the hydrogens described earlier in accordance with Balasubramanian et al., Chem. Phys. Lett. 164:231, 1989. Thus the Ga basis set is very flexible with a set of 3d polarization functions. There have been several theoretical studies on the electronic structure of Ga-containing species, the most recent by Schaefer and coworkers described in Xi et al., J. Am. Chem. Soc. 120:3773, 1998 which describes the possibility of a Ga—Ga triple bond in organometallic complexes. All computations were carried out using Gaussian 94 package of codes by Frisch et al., Gaussian 94, Revision C.2, Pittsburgh, Pa., 1995.

$GaH_3$ and $GaH_2$ molecules were chosen as tractable models to compute the normal mode frequencies of these species. At the MP2 level of theory the $GaH_3$ planar molecule ($D_{3h}$) with $^1A_1$ ground state has $A_1$ and E stretching modes with the frequencies of 2011.6 and 1988.8 cm$^{-1}$, respectively. The IR intensities of the E and $A_1$ modes are 238.3 and 0.0, respectively in the $D_{3h}$ symmetry. The MP4 level of theory yields slightly lower (5% ) frequencies. The bending frequencies are 770 and 815 cm$^{-1}$, respectively for the $A_2$ and E modes. The IR intensities are 241 and 181, respectively. The MP4 and MP2 bending frequencies are very close (within 2–7 cm$^{-1}$). The $GaH_2$ triatomic has a $C_{2v}$ structure with a $^2A_1$ ground state. Since the trivalency of Ga is not fully satisfied in this radical, it has lower vibrational frequencies. At the MP2 level of theory the $A_1$(symmetric) and $B_2$ (asymmetric) Ga—H stretches have vibrational frequencies of 1811 and 1848 cm$^{-1}$, respectively, while the $A_1$ bending mode has a frequency of 805.1 cm$^{-1}$. The computed IR intensities are 343 and 66 for the $B_2$ and $A_1$ stretching modes, while it is 160 for the bending mode.

Figure 9A:
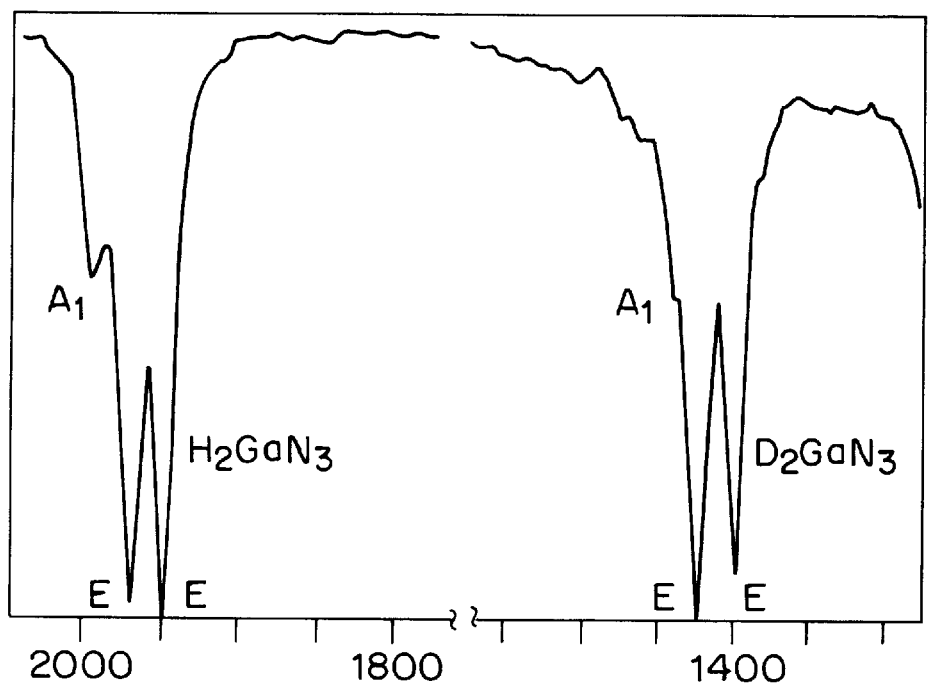
FIG. 9 is a segment of an IR spectrum of the [Ga—H, (D)] stretching modes and the corresponding [H—Ga—H, (D)] bending modes.
Figure 9B:
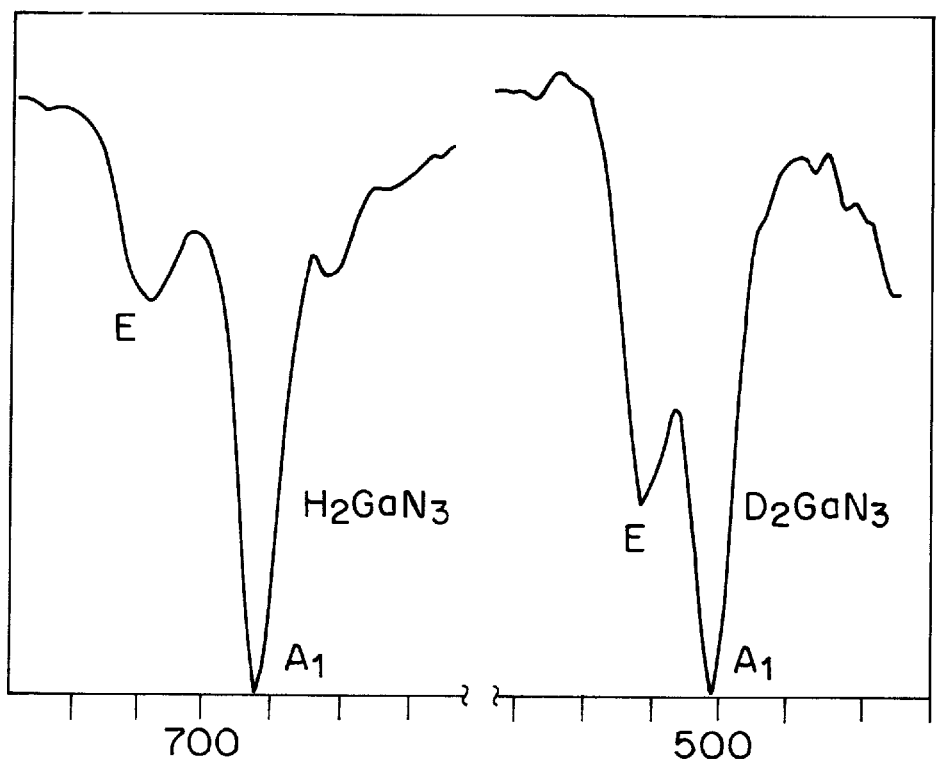

The above symmetry and quantitative analysis reveals that there are two possibilities for the assignment of the three bands in the 1950–2000 cm$^{-1}$ region of the observed spectrum. As discussed earlier, the Ga—H stretching modes for the trimer ($H_2GaN_3$) yield two $A_1$ and two E normal modes all of which are expected to be IR active. On the basis of the computed vibrational frequencies for $GaH_3$ stretching modes, it was determined that the E mode has a slightly lower frequency (1988.8 cm$^{-1}$)than the $A_1$ (2011.6 cm$^{-1}$). However, for the trimer, since there are three $GaH_2$ groups, the two E stretching modes would interact since their symmetries are the same and their frequencies are expected to be very close. Furthermore, on the basis of computed results, the E peaks would have substantially larger IR intensities compared to $A_1$. Thus the two peaks with higher intensities for the protonated compound $H_2GaN_3$ at 1950 cm$^{-1}$ and 1973 cm$^{-1}$ are tentatively assigned to the two Ga—H stretching modes of E symmetry of the trimer. The other lower intensity peak at 1997 cm$^{-1}$ is due to the $A_1$ stretching mode in which all three Ga—H bonds pointing up (likewise the three bonds down) move in the same direction in a coherent manner as in a breathing mode. Note that for the planar $D_{3h}$ $GaH_3$ structure, this mode has zero IR intensity and is not IR-active but for the non-planar $C_{3v}$ structure this mode would appear but with reduced intensity compared to the E mode. This analysis is fully consistent with the observed frequency and relative intensity of the band at 1997 cm$^{-1}$ shown in FIG. 9.

The $(H_2GaN_3)_2$ dimer has only two IR-active Ga—H stretching modes with $B_{1u}$ and $B_{2u}$ symmetry. The vapor IR spectrum of the structurally analogous gallane ($Ga_2H_6$) indeed reveals only two peaks in the higher-frequency stretching region near 1980 cm$^{-1}$. In contrast the IR spectrum of this sample displayed at least three prominent peaks in the high frequency region and another weak peak may also be present near 2000 cm$^{-1}$. These peaks cannot only be due to a pure dimer although the possibility of a dimer-trimer mixture cannot be entirely eliminated. However, on the basis of this analysis, it appears that the spectrum is most likely due to the trimeric $[H_2GaN_3]_3$ which is expected to display two strong closely-spaced E modes and in addition two weaker $A_1$ modes. The E modes and at least one of the A modes in this spectrum were observed.

The low frequency modes in the 665–725 cm$^{-1}$ region can be assigned to the H—G—H bending modes. The computed vibrational frequencies of the $A_1$ and E bending modes of $GaH_3$ favor this assignment. There are three such H—G—H bonds for the trimer and they correspond to $A_1$ and E modes. The two bands at 720 and 685 cm$^{-1}$, are assigned to the E and $A_1$ bending modes respectively. The other very weak band at 663 cm$^{-1}$, may be due to a ring-shearing mode or a Ga—N type mode. As previously noted herein the vibrational data and corresponding assignments are summarized in Table 5.

The Raman spectra of the observed species and more detailed computational analysis of the actual trimer are performed according to standard techniques. If the dimer were to be present in the sample, the Raman spectrum should show two new stretches corresponding to $A_g$ and $B_{3g}$ Raman active modes, while the IR active $B_{1u}$ and $B_{2u}$ modes should disappear. On the other hand, all modes are Raman active for the trimer.

EXAMPLE 6

STABILIZATION OF $H_2GaN_3$ WITH $C_5H_5N$ AND $NME_3$ (TMA)

Neat $H_2GaN_3$ in the absence of solvents is a highly reactive substance. Although the compound is stable at room temperature, abrupt scraping of the sample can initiate a vigorous decomposition via loss of $N_2$ and $H_2$ to yield pure GaN. It is, therefore, of immediate interest to increase its stability by coordination of the unsaturated monomeric units of the compound with Lewis bases to form potentially less reactive adducts that could lead to a new class of GaN precursors. A survey of reactions between $H_2GaN_3$ with selected Lewis bases such as $C_5H_5N$ and $NMe_3$ (TMA) are described below.

A pyridine complex is readily prepared as a mobile liquid by direct interaction of the compound with an excess of dry $C_5H_5N$ as follows.

$H_2GaN_3$ (0.50 g, 4.40 mmol) were combined with an excess of dry $C_5H_5N$ at 0° C. The reaction mixture was stirred at room temperature for 2 hours under nitrogen and then the unreacted $C_5H_5N$ was removed under vacuum to yield 6 as a mobile liquid. IR(thin film): 3118–300(w), 2093(vs), 1917(s), 1614(s), 1454(s), 1349–1296(m), 1072–1020(m), 763–643(s), 495(m), 411 (m). $^1H$ NMR (toluene-$d_8$ 22° C.): δ5.38 for Ga—H and resonances corresponding to the coordinated $C_5H_5N$: 8.50 (d, 2H), 6.77 (t, 1H), 6.38 (m, 2H). The complex is more stable than the uncoordinated $H_2GaN_3$, however attempts to distill the product at low pressures and T>40° C. resulted in the disproportionation of the adduct. The complex is identified by its spectroscopic properties. The $^1$H NMR spectrum of the adduct at 22° C. reveals a broad resonance at δ5.37 which is shifted significantly from that of the pure compound (δ4.81). The spectrum at −50° C. displays a considerably sharper singlet at δ5.46 which is only shifted slightly with respect to the 22° C. peak. The resonances corresponding to the pyridine protons are also present in the spectrum and are significantly shifted with respect to free pyridine. For example, the resonance of the ortho hydrogens for the coordinated pyridine group has shifted upfield by 0.7 ppm with respect to that of free pyridine dissolved in toluene-d$_8$. Integration of the signals consistently suggests a composition of H$_2$GaN$_3$.C$_5$H$_5$N. The IR spectrum confirms the presence of coordinated pyridine and shows that the frequencies of the asymmetric stretches for the azide (2086 cm$^{-1}$) and Ga—H (1916 cm$^{-1}$) have shifted to lower frequencies with respect to those of H$_2$GaN$_3$, which are observed at 2129 cm$^{-1}$ and 1971 cm$^{-1}$, respectively. The H$_2$GaN$_3$.C$_5$H$_5$N compound is considerably more stable than pure H$_2$GaN$_3$.

H$_2$GaN$_3$ also reacts readily with an excess of trimethylamine to yield a volatile colorless liquid which is isolated by trap-to-trap distillation as follows.

Dry trimethylamine (0.37 g, 6.2 mmol) was combined at −196° C. with (0.600 g, 5.25 mmol) of H$_2$GaN$_3$. The reaction mixture was stirred at room temperature for 2 h under nitrogen and then evacuated to eventually obtain a mobile liquid which was purified by trap-to-trap distillation from 22° C. to −20° C. IR(thin film): 2983–2850(m), 2101 (vs), 1908(s), 1475(s), 1346(m), 1293(m), 1111(m), 1004(s), 731(s), 683(s), 496 (m), 412 (m). EIMS (m/e): 171 (M$^+$-H), 130 (M$^+$-N$_3$). $^1$H NMR (toluene-d$_8$): δ1.60, and δ4.95 at 22° C. This product was identified by its spectroscopic properties to be the molecular adduct H$_2$GaN$_3$.NMe$_3$. The $^1$H NMR spectrum shows two singlets, one sharp at δ1.60 and the other broad at δ4.95, corresponding to the protons of the NMe$_3$ and GaH$_2$ components of the adduct, respectively. The compound is volatile in the mass spectrometer and the highest mass peak at 171 amu is attributable to the monomer H$_2$GaN$_3$.NMe$_3$. The calculated isotopic pattern is in agreement with the experiment and supports the formation of the adduct. The IR spectra indicate a Lewis acid-base compound between H$_2$GaN$_3$ and NMe$_3$ and the data are consistent with the well established IR properties of the related Me$_3$N.GaH$_3$ as described in Pulham et al., J. Am Chem. Soc. 113:5149–5162, 1991. The frequencies of the asymmetric stretches for the azide (2100 cm$^{-1}$) and Ga—H (1908 cm$^{-1}$) have shifted to lower frequencies with respect to those of H$_2$GaN$_3$, (ν(N$_3$)2129 cm$^{-1}$, ν(Ga—H) 1971 cm$^{-1}$).

EXAMPLE 7

DEPOSITION STUDIES WITH HClGaN$_3$

The compound HClGaN$_3$ is stable with respect to loss of HCl and N$_2$ at room temperature. It is insensitive to shock but it decomposes exothermically at the melting point (70° C.) via displacement of N$_2$ and HCl to yield a light gray solid. The decomposition occurred very rapidly with release of large amounts of heat, and often with spontaneous ignition. The remaining solid was identified by powder X-ray diffraction and by IR examination to be nanocrystalline GaN. The IR spectra illustrated a broad peak at 560 cm$^{-1}$ corresponding to Ga—N lattice vibrations and showed no detectable azide, Ga—H, N—H, and O—H absorptions. Complementary transmission electron microscope studies confirmed that the material was nanocrystalline, with a mixture of cubic and hexagonal GaN grains.

This precursor was volatile in the mass spectrometer at room temperature and the spectrum indicated that the vapor consisted of the trimer [HClGaN$_3$]$_3$ Vapor deposition studies were performed and initial results clearly showed that the thermal decomposition of the vapor on sapphire substrates at 500–550° C. resulted in formation of stoichiometric GaN. Relatively low chlorine contamination (0.5 at. %) was found for films grown at and below 500° C. but higher deposition temperatures (600° C.) provided material free of chlorine impurities.

EXAMPLE 8

DEPOSITION OF GaN FROM H$_2$GAN$_3$

In order to evaluate the feasibility of H$_2$GaN$_3$ as a viable precursor to GaN, a series of growth experiments were performed in an ultra-high vacuum (UHV) CVD system. The molecule was held in a glass reservoir at room temperature directly attached to the reactor and the vapor of the compound was simply allowed to flow into the vacuum system which was typically maintained at a base pressure of 10$^{-10}$ Torr by a corrosion resistant turpopump. A rise in pressure from 10$^{-10}$ to approximately 2×10$^{-6}$ Torr was immediately established from the room-temperature vapor pressure of the compound. With direct vaporization of the precursor at 22° C. and at substrate temperatures between 200 and 800° C., a range of GaN samples were grown at remarkably high growth rates of 600–800 Å per minute. Films of thicknesses ranging from 15000 Å to 7000 Å were readily grown within ten to fifteen minutes of deposition time. A residual gas analyzer attached downstream from the reaction zone provided information about the volatile byproducts. The mass spectra of the residual gasses were clean and simple. The only mass peaks observed are at 2, 14, and 28 amu and are due to H$_2$ and N$_2$ as indicated in the proposed decomposition reaction depicted by the following reaction:

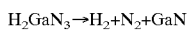

H$_2$GaN$_3$→H$_2$+N$_2$+GaN

Mass peaks associated with the precursor were not detected even at highest sensitivities.

Figure 10:
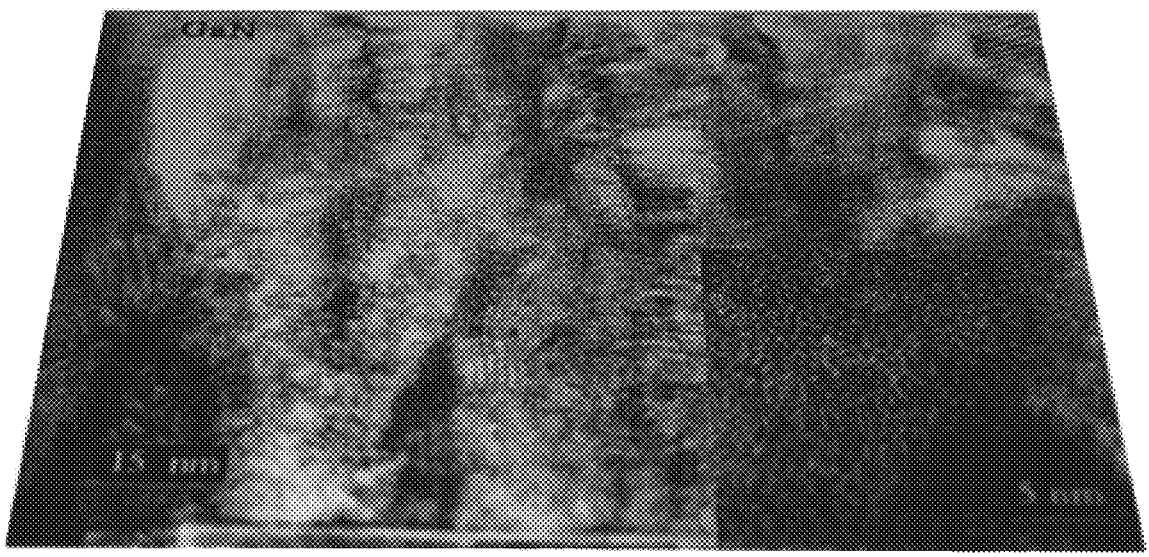
FIG. 10 is a cross-sectional electron micrograph showing columnar growth of a GaN layer formed by the thermal decomposition of $H_2GaN_3$.
Figure 11:
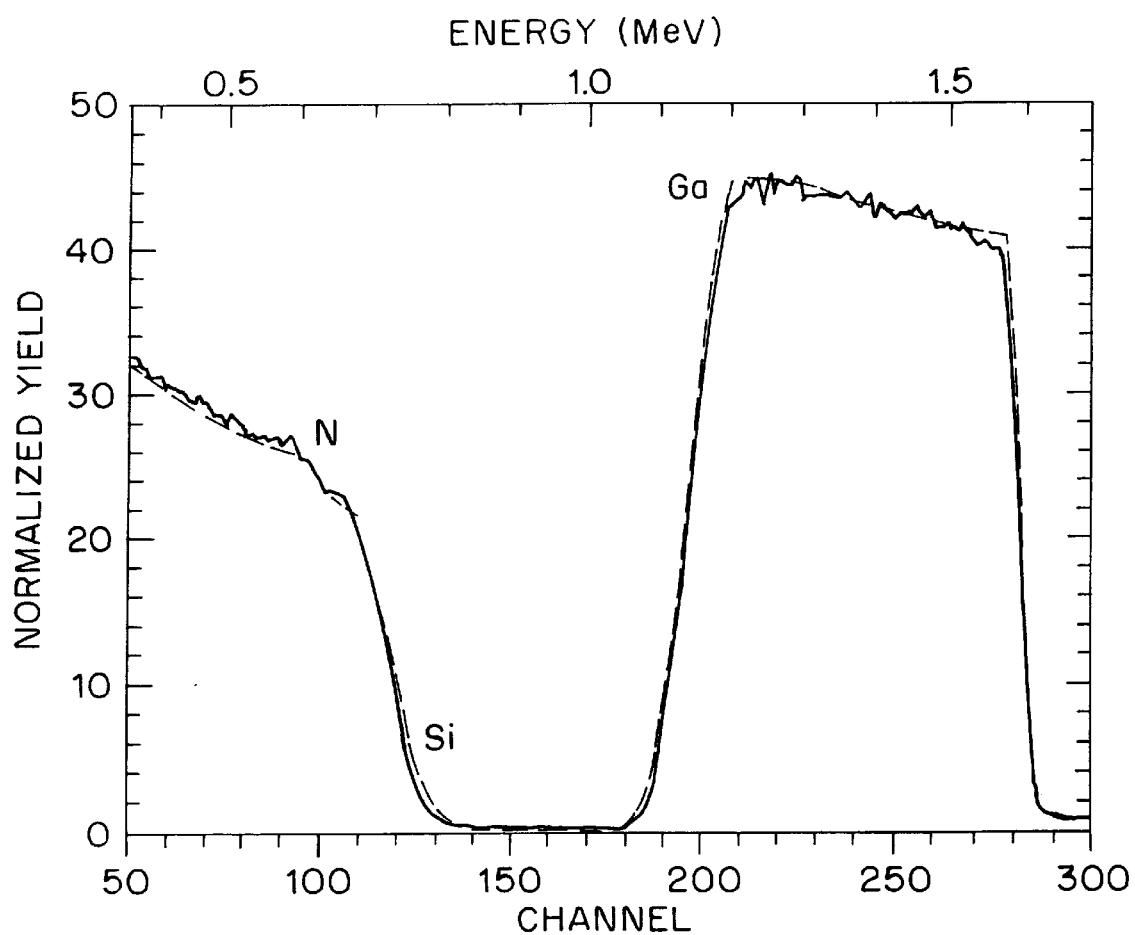
FIG. 11 is the RBS spectrum of GaN grown at 300° C. on (100) Si.

Cross-sectional high-resolution electron microscopy of samples deposited on Si revealed columnar growth of the wurtzite phase, illustrated in FIG. 10, for a layer grown at 500° C. Microscopic examinations of the 200° C. and 300° C. samples revealed that the films were smooth and highly coherent. High resolution images revealed that the samples consisted of nanocrystallites evenly distributed throughout the layer. The only feature displayed in the transmission IR spectrum of the same sample was a band at 560 cm$^{-1}$ which is consistent with GaN. Vibrational modes characteristic of Ga—H and N$_3$ moieties were absent from the spectrum confirming that complete decomposition of the precursor has occurred 200° C. The composition of the films was routinely checked by Rutherford backscattering spectroscopy (RBS) as illustrated in FIG. 11 including nitrogen, carbon, and oxygen resonance reactions to determine the Ga—N stoichiometry and levels of impurities. The analyses yielded stoichiometric nitride material free of oxygen and carbon contaminations. Auger electron spectroscopy depth profiles confirmed that the material is indeed pure. These results demonstrate that growth of pure but nanocrystalline GaN is possible at 200° C. and 10$^{-6}$ Torr via the thermodynamically driven decomposition of H$_2$GaN$_3$. Crystalline GaN material is readily obtained at higher growth temperatures.

EXAMPLE 9

FILM GROWTH USING H$_2$GaN$_3$

Figure 12:
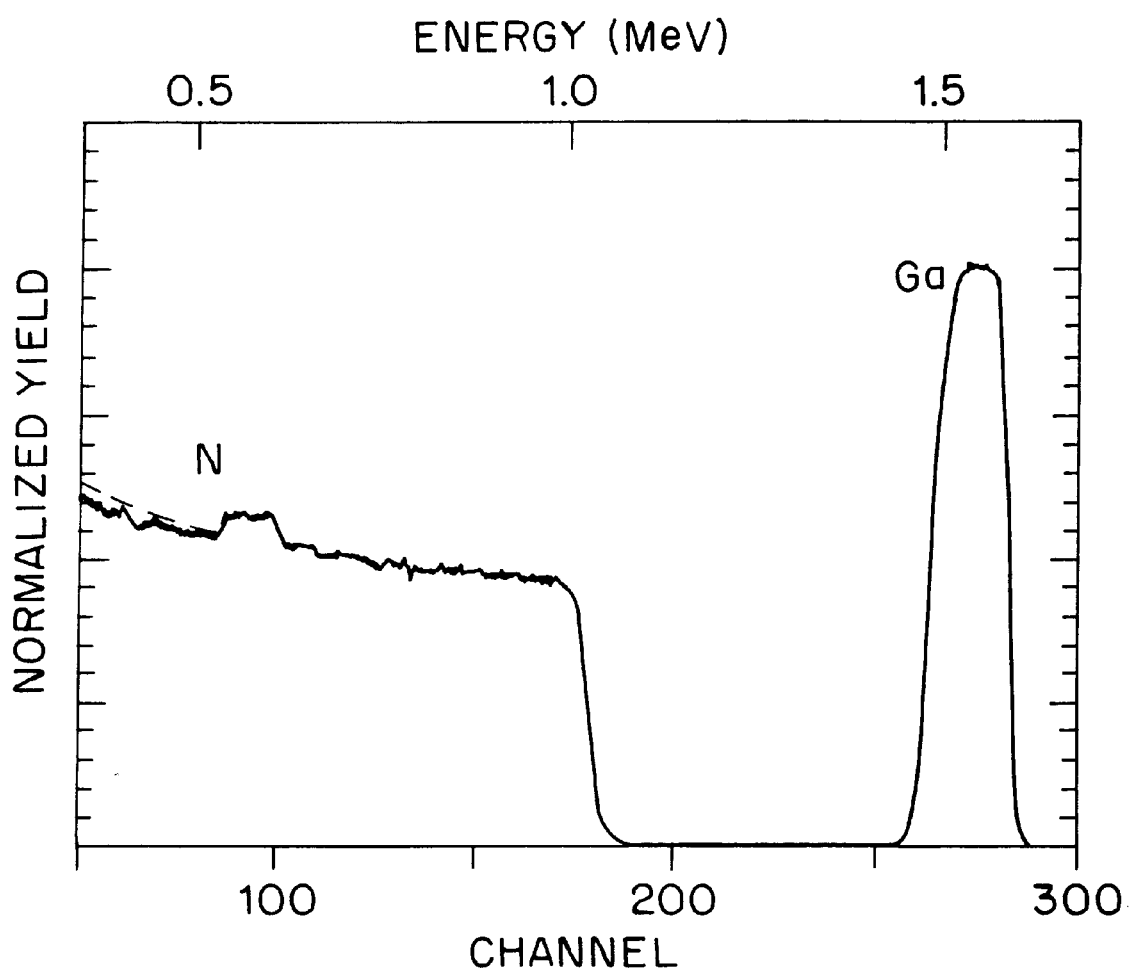
FIG. 12 is the 2 MeV He$^{2+}$ RBS spectrum of GaN on (100) Si.
Figure 13:
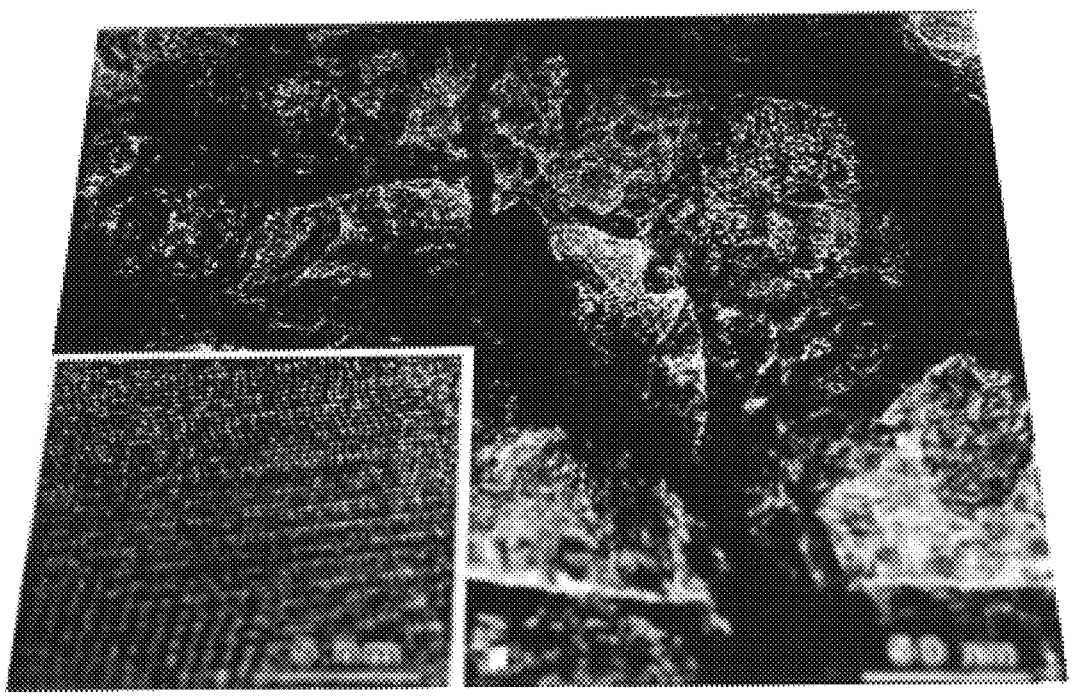
FIG. 13 is an electron micrograph of GaN powder.

Initial results indicate that H$_2$GaN$_3$ in its pure form is extremely reactive at room temperature. Its decomposition, frequently induced by scraping the sample in the dry box by a glass or metal rod, is very characteristic of a self-sustaining exothermic reaction rather than a detonation. This high reactivity made it impossible to obtain combustion analysis, although the decomposition byproducts were characterized as described below. The compound was nevertheless easily handled in solution and its role as a potential precursor to GaN thin films and bulk materials was explored. Depositions on Si substrates were performed by direct vaporization of the compound in an ultrahigh-vacuum chemical vapor (UHV-CVD) deposition system to illustrate the feasibility of the molecule as a CVD precursor. Film growth was obtained at $2-4\times10^{-4}$ Torr and 450° C. with a deposition rate of 12 nm/min. Rutherford backscattering (RBS) analysis illustrated in FIG. 12 including carbon, oxygen, and nitrogen resonance reactions reveal pure and stoichiometric GaN material. Cross-sectional high resolution TEM observations showed growth of columnar grains, typically about 50 nm wide, that extended from the interface through the entire layer and consisted of completely crystalline material. Both wurtzire and zincblende regions could be identified from their characteristic stacking sequences. The most noteworthy result is that extensive crystallinity was observed, i.e., no amorphous areas were found, for this material which is not epitaxial since it is grown on native Si oxide and below 450° C., as shown in FIG. 13.

Figure 14A:
FIGS. 14(a) and 14(b) are a cross sectional electron micrograph growth of mixed cubic and hexagonal phases of GaN on the substrate and a high magnification image showing growth of wurtzite phase close to the substrate, respectively.
Figure 14B:
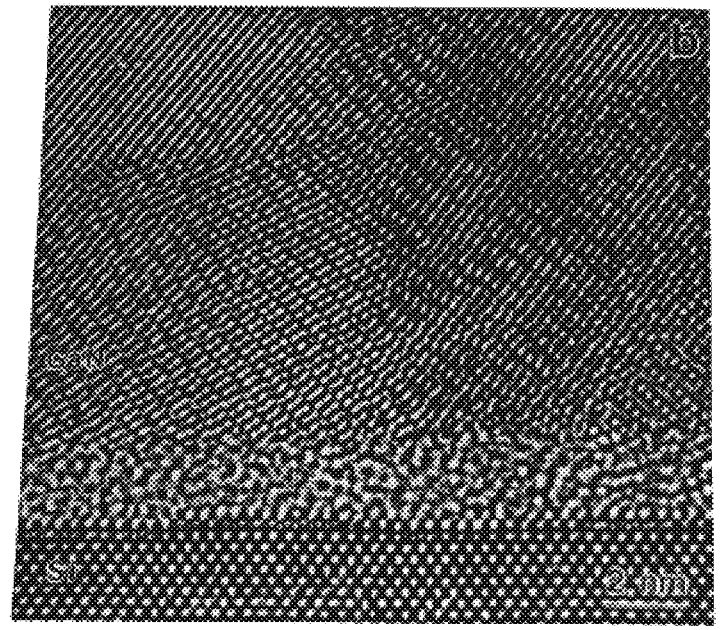

Equally fascinating was the unusual morphology and microstructure of the highly-pure bulk GaN material obtained from the rapid decomposition of the precursor often initiated at or near room temperature in the dry box. As shown in FIGS. 14(a) and 14(b) the material is composed of a light yellow network of interconnected microfibers up to several microns in length and 15–20 nm wide that consist of crystallites oriented along the fiber axis. Interestingly, there was no observation of any amorphous component by TEM neither at the grain boundaries nor in the bulk of the fibrous material. The individual grains which ranged from 15–20 nm in size were primarily hexagonal GaN, although disordered regions and some of the cubic phase were also found. The polycrystalline character of this high aspect ratio product and the presence of the cubic and hexagonal phases were confirmed by X-ray diffraction studies which also demonstrated the preferential orientation of the crystallites. The only feature displayed in IR spectra was a remarkably sharp band at 560 cm$^{-1}$ consistent with crystalline GaN. The lack of O—H modes in the IR spectra even after prolonged exposures (several weeks) to air demonstrates the high stability of this high surface area material. Furthermore, energy dispersive X-ray analysis in a field emission gun microscope did not show any chlorine contamination indicating that the precursor did not contain chlorine impurities.

Annealing of the microfibers at 800° C. produced a completely white powder that was found to be wutizitic GaN by powder diffraction. Photoluminescence studies show that the annealed material luminescences at about 3.3 eV whereas the unannealed sample emits in the visible (1.92 eV) and and UV regions (3.28 eV).

EXAMPLE 10

DEPOSITION OF GaN USING H$_2$GaN$_3$ USING HOT WALL REACTOR

Figure 15A:
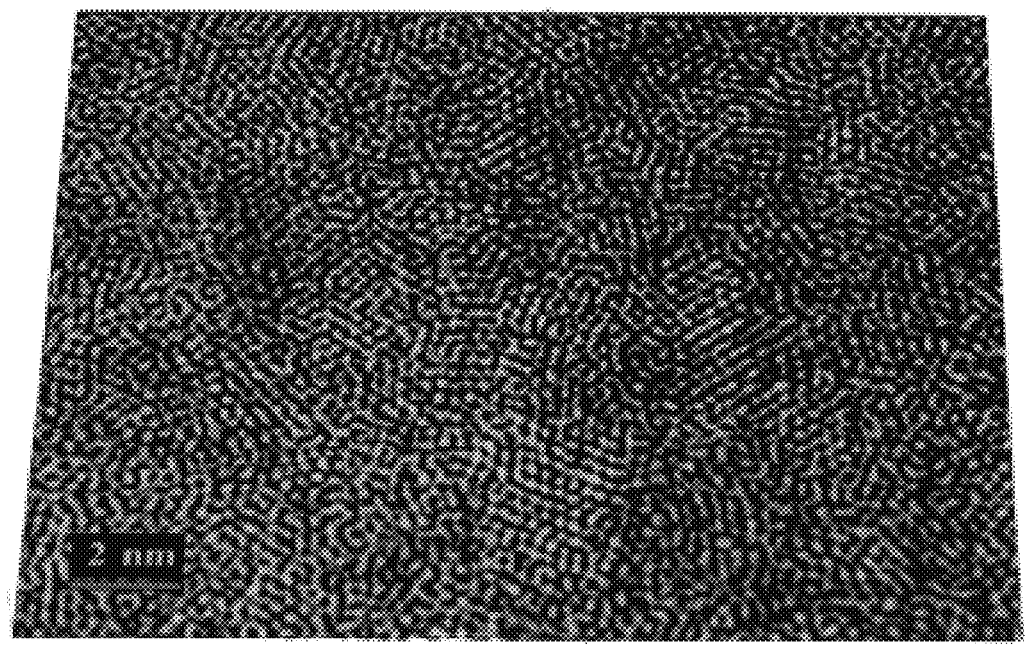
FIGS. 15(a) and 15(b) are an electron micrograph showing an enlarged portion of GaN layer grown at 200° C., and the corresponding X-ray diffraction pattern thereof, respectively.
Figure 15B:
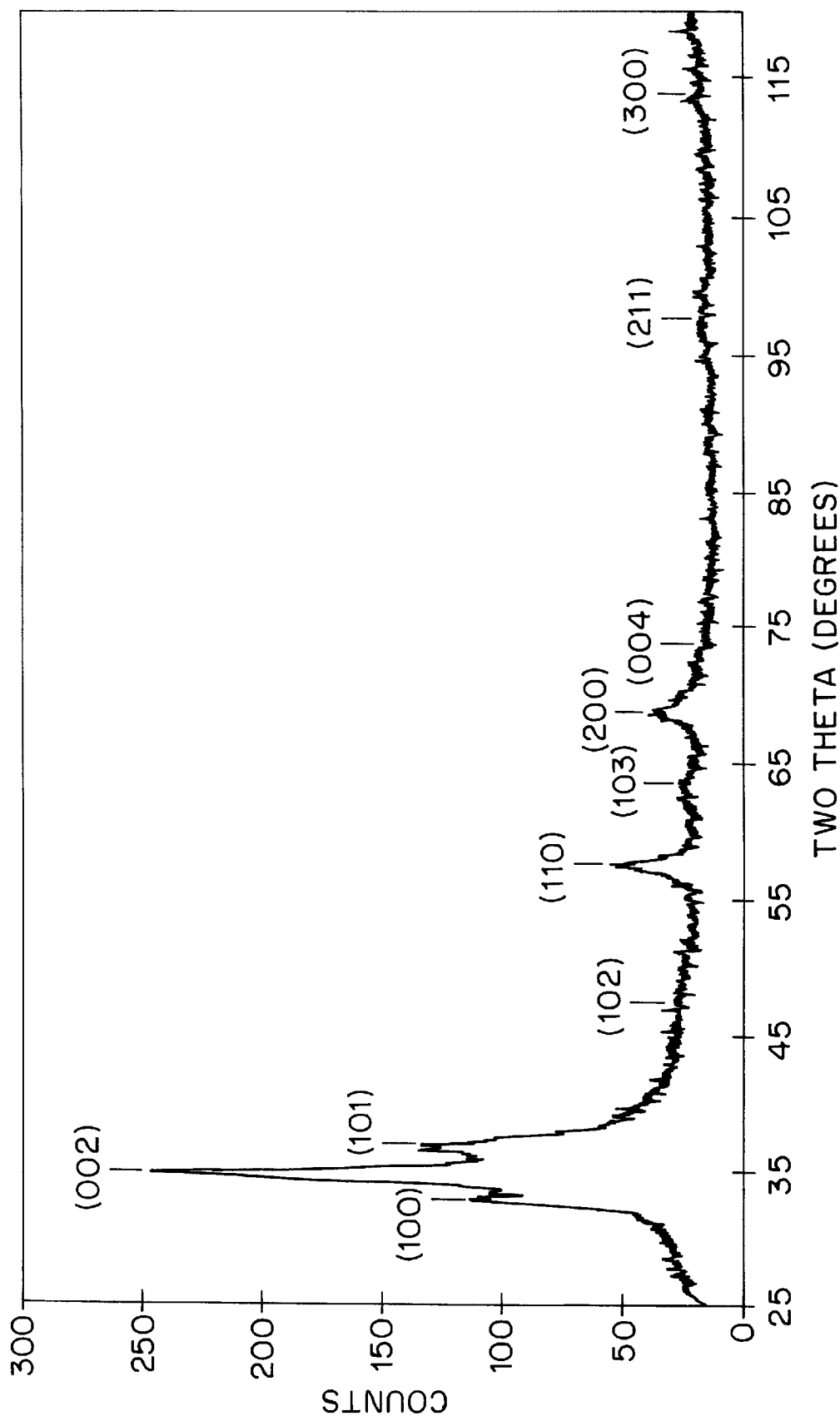

The first successful deposition of pure GaN via H$_2$GaN$_3$ was readily accomplished at 150–200° C. on (100) Si using a hot-wall UHV-CVD reactor described in Todd et al., Appl. Phys. Lett., 67:1243, 1995. The precursor, held in a glass reservoir directly attached to the reactor, vaporized readily at room temperature and was transported at a remarkably steady rate onto the growth surface at 10$^{-4}$ Torr pressure. It was not necessary to have large conductances between the source and the substrate or to heat the source in order to obtain acceptable growth rates. Films ranging in thickness from 120 to 200 nm were obtained at 200° C. with an average growth rate of 30 nm per minute. Rutherford backscattering (RBS) including C, N and O resonance reactions and forward scattering revealed stoichiometric GaN free of any carbon, oxygen and hydrogen impurities. Fourier transform infrared (FTIR) analysis of samples deposited on Si confirmed the complete lack of hydrogen in the film, i.e., no Ga—H or N—H vibrations were observed. Cross sectional transmission electron micrographs and diffraction patterns revealed nanocrystals typically 2–3 nm in size, which were evenly distributed throughout the layer as shown in FIG. 15a. Complementary X-ray diffraction studies performed on a thin film Guinier diffractometer with a fixed incident angle of 4° confirmed that the material was nanocrystalline and demonstrated some degree of crystalline orientation. A representative diffraction pattern which is indexed as wurtzite GaN is shown in FIG. 15b. The synthesis of GaN nanocrystals with this method, which undoubtedly exploits the exothermic reactivity of H$_2$GaN$_3$, may provide a very simple chemical route to novel quantum dot structures. Such structures in bulk powder samples have been recently reported by Frank et al., Am. Chem. Soc., 120:3512, 1998 to exhibit a blue shifted (4.2 eV) high energy emission.

EXAMPLE 11

OPTIMIZATION STUDIES OF DEPOSITION USING H$_2$GAN$_3$ IN THE UHV-CVD SYSTEM

Figure 16A:
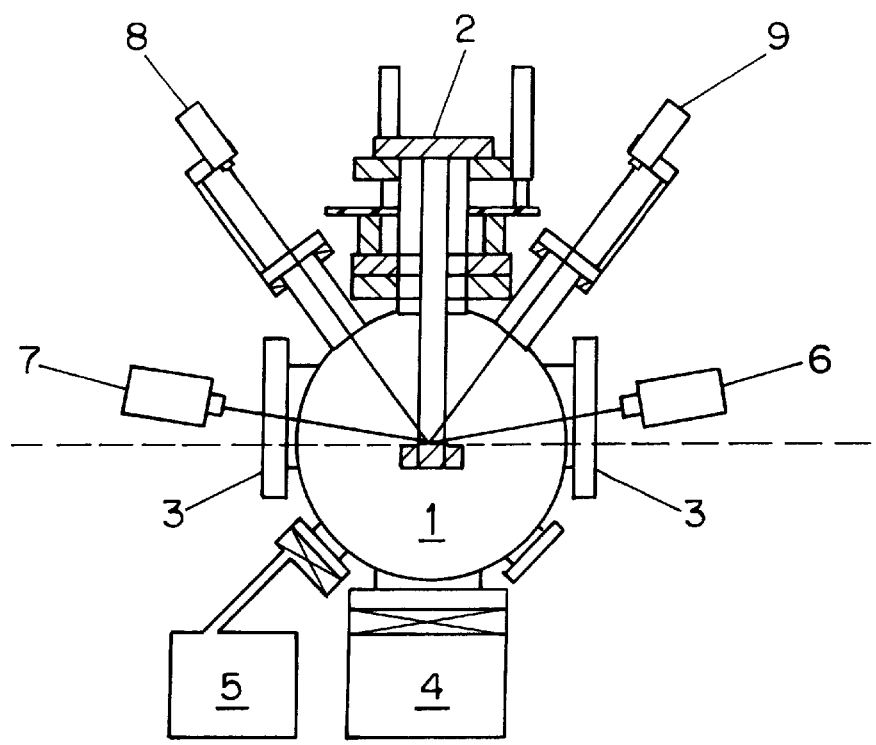
FIG. 16(a) and (b) respectively are a schematic illustration of an UHV-CVD chamber with in situ diagnostics and in situ diffraction pattern of GaN grown at 500° C., respectively.

In order to establish deposition conditions that optimize production of the desired material especially at conditions of pressure and temperature that are comparable with those of classical growth via molecular beam epitaxy (MBE), a series of experiments were performed on (100) Si substrates using an advanced ultrahigh-vacuum (UHV) CVD system. In this system, a CVD-compatible chamber is interfaced with three techniques which are intended to monitor, diagnose, and analyze the film growth under the hostile conditions found in CVD. The first technique is X-ray reflectivity which is used to obtain film thickness as well as interface and surface roughness. The second is laser multiple-beam optical stress sensing (MOS) which is applicable for measurement of any mechanical stress which is built up in films during growth as well as determining growth rates and variations in thickness. The third technique is conventional X-ray diffraction of the deposited material by use of the characteristic K$_\alpha$ radiation of Ag. The vacuum chamber, illustrated in FIG. 16a, is located on the theta-theta axis of the goniometer of a custom designed X-Ray diffractometer, and is equipped with Be windows (3) that transmit the incoming and diffracted beams. Very accurate sample alignment is maintained by a series of computerized stepper motors. The detailed illustration in FIG. 16(a) shows the UHV-CVD chamber with in situ diagnostics featuring the substrate (1), computerized stages for substrate alignment (2) Be windows (3) turbo pump (4), process turbo (5), X-ray detector (6), silver anode (7), diode laser (8) and CCD detector (9).

The precursor H$_2$GaN$_3$ was held in a glass container at room temperature and directly connected to the reaction chamber with a high vacuum valve. The portion of the reactor leading from the reservoir into a resistively-heated boron nitride substrate holder inside the reactor was held at 22° C., and the vapor of the compound was allowed to flow into the vacuum system which was typically maintained at a base pressure of 10$^{-10}$ Torr by a corrosion resistant turbopump (4). A rise in pressure from 10$^{-10}$ to approximately 2×10$^{-6}$ Torr was immediately established from the room-temperature vapor pressure of the compound. No carrier gas was used. The pressure remained constant during the course of the experiment despite the low conductance due to narrow inlet lines and small-orifice valves used. Under these conditions, direct vaporization of the precursor at 22° C., and at substrate temperatures between 250 and 800° C., a range of GaN samples was grown at remarkably high growth rates. The rate of deposition was dependent principally on the substrate temperature and was not limited by mass transport. Maximum rates of 60–80 nm per minute were obtained at the lower temperatures of 250–700° C., but a marked decrease in growth rate to nearly 20 nm per minute, and a substantial barrier in nucleation, was observed at a temperature greater than 800° C. on Si substrates. Films of thicknesses ranging from 700 nm to 2 $\mu$m were readily grown with deposition times of ten to twenty-five minutes. A residual gas analyzer attached downstream from the reaction zone provided information about the volatile byproducts. The mass spectra of the residual gasses were clean and simple. The only mass peaks observed were at 2, 14, and 28 amu. These are due to $H_2$ and $N_2$ as indicated in the proposed decomposition reaction depicted by the following equation:

$$H_2GaN_3 \rightarrow H_2 + N_2 + GaN$$

Mass peaks associated with the precursor were not detected even at highest sensitivities.

Figure 16B:
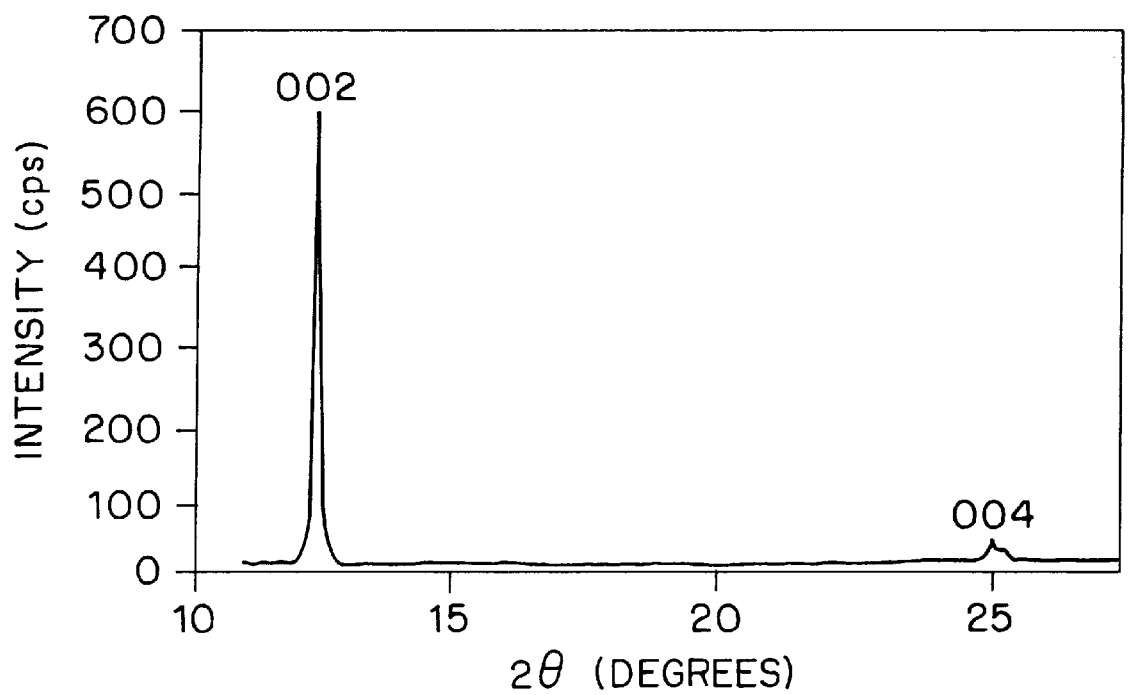
Figure 17A:
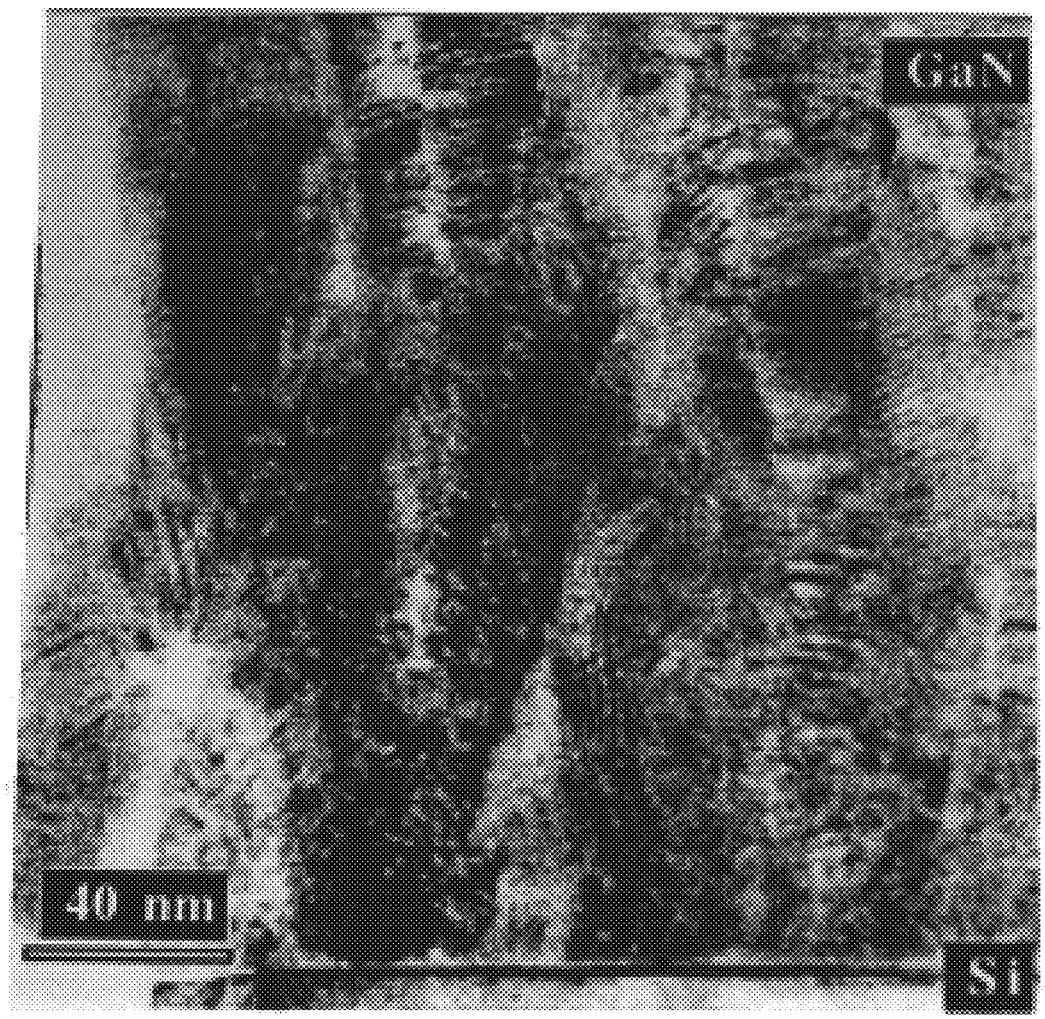
FIG. 17(a) and 17(b) are a cross-sectional electron micrograph showing columnar growth of GaN layer formed by thermal decomposition of H$_2$GaN$_3$ at 450–500° C. on Si (100), and a representative RBS spectrum from a sample grown at 500° C., respectively.
Figure 17B:
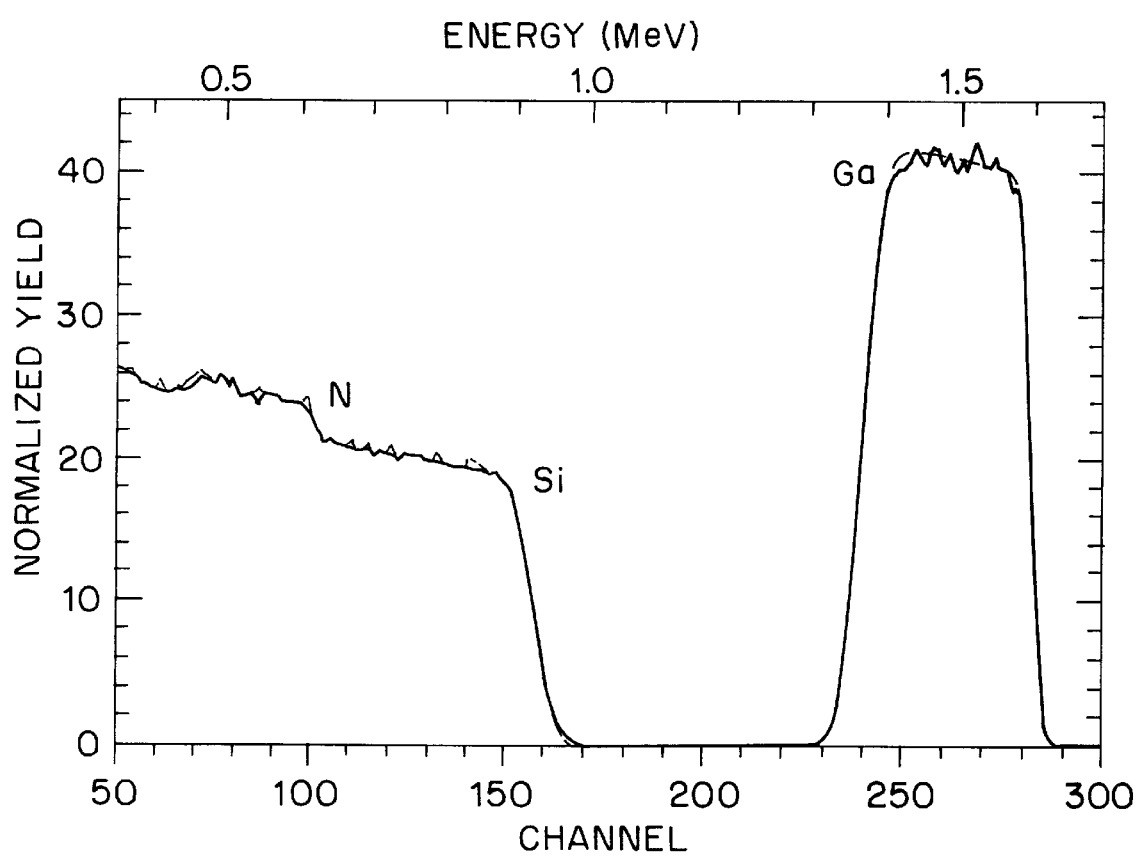

In situ X-ray diffraction experiments revealed that samples grown at 250° C. were poorly crystallized. Microscopic examinations revealed that the films were smooth and highly coherent, i.e., free of voids. High resolution electron micrographs showed nanocrystallites evenly distributed throughout the layer similar to that shown in FIG. 15a. The only feature displayed in the transmission IR spectrum of the same sample was a band at 560 cm$^{-1}$ which is consistent with GaN. Vibrational modes characteristic of Ga—H and $N_3$ moieties were absent from the spectrum confirming that complete decomposition of the precursor has occurred 250° C. The composition of the films was routinely checked by RBS including nitrogen, carbon, and oxygen resonance reactions to determine the Ga—N stoichiometry and impurity levels. The analyses yielded stoichiometric nitride material free of oxygen and carbon contaminations. Depth profiles by Auger electron spectroscopy and secondary ion mass spectrometric analysis (SIMS) confirmed the purity of the material. A high degree of crystallinity and orientation was observed in samples grown between 350 and 550° C., and highly oriented GaN material was obtained as the deposition temperature was increased to 500° C., as illustrated in FIG. 16(b). Complementary cross-sectional high-resolution electron microscopy of samples deposited on Si revealed columnar growth of the wurtzite phase for a layer grown at 500° C. as shown in FIG. 17a.

Figure 18:
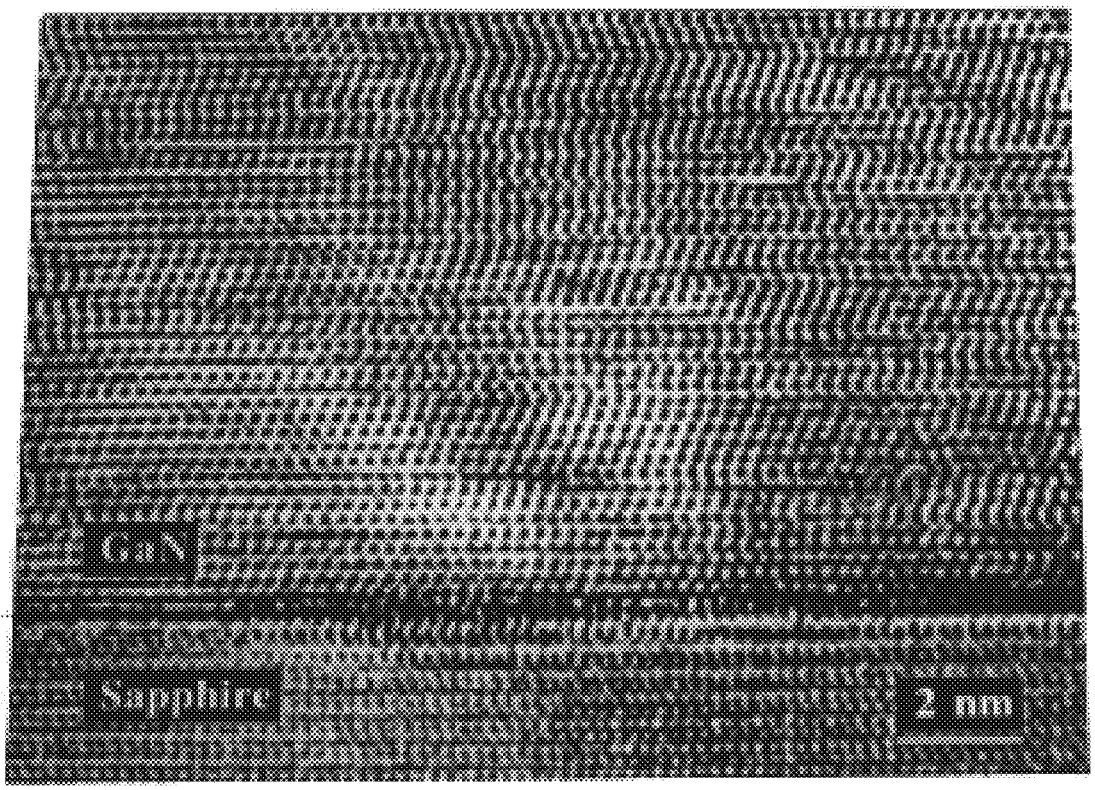
FIG. 18 is a high-resolution cross-sectional electron micrograph showing heteroepitaxial growth of wurtzite GaN on sapphire at 650° C.

The possibility of epitaxial growth on sapphire substrates was also investigated. These depositions were carried out at 650–700° C. and at reaction pressures of 10$^{-6}$ Torr with corresponding growth rates comparable to those observed for depositions on Si. RBS and SIMS analyses again revealed stoichiometric GaN free of impurities. FIG. 18 is a high-resolution cross-sectional-electron micrograph showing the initial growth of disordered wurtzite GaN deposited on sapphire at 650° C. Selected-area electron diffraction indicates that some basic alignment of the material is obtained under these growth conditions but that substantial rotational disorder still exists.

Although the invention has been described herein with reference to specific embodiments, many modifications and variations therein will readily occur to those skilled in the art. Accordingly all such variations and modifications are included within the intended scope of the invention.

We claim:

1. A compound having the following general formula $$(X_1X_2GaN_3)_n$$

where $X_1$ and $X_2$ are the same or different and are selected from the group consisting of H and isotopes thereof, Cl, Br, F, I and $CH_3$ wherein when $X_1$ is $CH_3 X_2$ is H and wherein when $X_1$ is Cl $X_2$ is H and n=1, 2, 3 or 4.

2. A compound according to claim 1 wherein $X_1$ and $X_2$ are H and n=1.

3. A compound according to claim 1, wherein $X_1$ and $X_2$ are each individually an isotope of hydrogen selected from the group consisting of deuterium or tritium.

4. A compound according to claim 1 wherein $X_1$ is H, $X_2$ is Cl and n=1.

5. A compound according to claim 1 wherein $X_1$ is H, $X_2$ is selected from the group consisting of chlorine, bromine, fluorine, and iodine and n=1.

* * * * *

UNITED STATES PATENT AND TRADEMARK OFFICE
CERTIFICATE OF CORRECTION

PATENT NO. : 6,207,844 B1
DATED : March 27, 2001
INVENTOR(S) : Kouvetakis et al.

It is certified that error appears in the above-identified patent and that said Letters Patent is hereby corrected as shown below:

Column 22,
Line 30, "$CH_3X_2$" should read -- $CH_3$, $X_2$ --
Line 31, "Cl" should read -- Cl, --; and "$X_2$is" should read -- $X_2$ is --

Column 1,
Line 4, insert -- This invention was made with support from the National Science Foundation Contract DMR 9458047 and Army Research Organization Contract DAAHO 4-96-10229. Accordingly, the U.S. Government may have rights in the disclosed invention. --; and insert:
-- INTRODUCTION
The invention is directed to novel compounds which serve as single-source precursors for the deposition of gallium nitride on thin films. The invention is also directed to methods for the synthesis of these novel compounds. The invention is further directed to methods for the use of such compounds in the deposition of gallium nitride on thin films and in the synthesis of bulk materials. --

Column 2,
Line 30, "$CH_3X_2$" should read -- $CH_3$, $X_2$ --

Column 3,
Line 4, "cross sectional" should read -- cross-sectional --
Line 44, "$CH_3X_2$" should read -- $CH_3$, $X_2$ --

Column 4,
Line 1, "$H_2GaN_3.H_2GaN_3$" should read -- $H_2GaN_3$. $H_2GaN_3$ --
Line 8, "$N_3.H_2GaN_3$" should read -- $N_3$. $H_2GaN_3$ --
Line 14, "$HClGaN_3$," should read -- $HClGaN_3$ --
Line 16, "nanosize" should read -- nanosized --
Line 17, "$HCH_3GaN_3$," should read -- $HCH_3GaN_3$ --
Line 19, "torr is" should read -- torr, is --

UNITED STATES PATENT AND TRADEMARK OFFICE
CERTIFICATE OF CORRECTION

PATENT NO. : 6,207,844 B1
DATED : March 27, 2001
INVENTOR(S) : Kouvetakis et al.

Page 2 of 4

It is certified that error appears in the above-identified patent and that said Letters Patent is hereby corrected as shown below:

Column 6,
Line 56, "$\upsilon$" should read -- $\nu$ --

Column 7,
Line 20, "Lanalysis" should read -- analysis --
Line 30, "$(H_3C)_3SiN_3GaCl_3$" should read -- $(H_3C)_3SiN_3GaCl_3$ --
Line 59, "spectra includes" should read -- spectrum includes --
Line 60, "(N3)" should read -- $(N_3)$ --
Line 66, "quapiupolar" should read -- quadrupolar --

Column 8,
Line 4, "isostopic" should read -- isotopic --
Line 25, Table 1, "N(70" should read -- N(7) --
Line 40, Table 2, "a =" should read -- $\alpha$ = --
Line 43, Table 2, "Siemens $P_4$" should read -- Siemens P4 --
Line 44, Table 2, "20 = 12 " should read -- 2 = 12 --
Line 45, Table 2, "3_" should read -- 3 --
Line 52, Table 2, "$^aR = \Sigma(\|\ F_o| - |F_{c\|})/\Sigma|F_o|$." should read
-- $^aR = \Sigma(\|\ F_o| - |F_c\|)/\Sigma|F_o|$. --
Line 53, Table 2, "$^{1/2}$." should read -- $^{1/2}$ --

Column 9,
Line 25, "infared" should read -- infrared --
Line 28, "GA" should read -- Ga --
Line 29, "(m, $\rho$_Ga-H)" should read -- (m, $\rho$ Ga-H) --; and "(m, $\nu$_Ga-" should read -- (m, $\nu$ Ga- --
Line 30, "(m, $\delta$_M-N-M)." should read -- (m, $\delta$ M-N-M). --
Line 33, "obervation" should read -- observation --
Line 34, "(m/e):," should read -- (m/e): --
Line 53, "Ga." should read -- Ga, --

UNITED STATES PATENT AND TRADEMARK OFFICE
CERTIFICATE OF CORRECTION

PATENT NO.    : 6,207,844 B1
DATED         : March 27, 2001
INVENTOR(S)   : Kouvetakis et al.

It is certified that error appears in the above-identified patent and that said Letters Patent is hereby corrected as shown below:

Column 11,
Line 11, "an" should read -- a --
Line 30, Table 3, "$]^{1/2}$," should read -- $]^{1/2}$, --
Line 56, "NgaN" should read -- NGaN --

Column 14,
Lines 11-12, Table 5, "ν(Ga-h)E" (both occurrences) should read -- ν(Ga-H)E --
Line 16, Table 5-footnote, "assignment" should read -- assignment --

Column 15,
Line 3, "modes all" should read -- modes, all --
Line 28, "$^1A_1$" should read -- $^1A_1$ ´ --; and "E" should read -- E´ --
Line 30, "E" should read -- E´ --; and "$A_1$" should read -- $A_1$´ --
Line 34, "$A_2$" should read -- $A_2$´ --; and "E" should read -- E´ --

Column 16,
Line 20, "H-G-H" should read -- H-Ga-H --
Line 21, "$A_1$" should read -- $A_1$´ --; and "E" should read -- E´ --
Line 41, "$NME_3$" should read -- $NMe_3$ --

Column 17,
Line 48, "(ν($N_3$)" should read -- (ν($N_3$)) --

Column 18,
Line 11, "$H_2GAN_3$" should read -- $H_2GaN_3$ --
Line 19, "turpopump." should read -- turbopump. --

Column 19,
Line 20, "wurtzire" should read -- wurtzite --
Line 49, "¶Annealing" should read -- Annealing --
Line 50, "wutizitic" should read -- wurtzitic --
Line 54, "and" (second occurrence) should be deleted

UNITED STATES PATENT AND TRADEMARK OFFICE
CERTIFICATE OF CORRECTION

PATENT NO.   : 6,207,844 B1
DATED        : March 27, 2001
INVENTOR(S)  : Kouvetakis et al.

It is certified that error appears in the above-identified patent and that said Letters Patent is hereby corrected as shown below:

Column 20,
Line 10, "Cross sectional" should read -- Cross-sectional --
Line 29, "H₂GAN₃" should read -- $H_2GaN_3$ --

Signed and Sealed this

Eighteenth Day of December, 2001

Attest:

Attesting Officer

JAMES E. ROGAN
Director of the United States Patent and Trademark Office